US012729397B2

(12) United States Patent
Berka et al.

(10) Patent No.: US 12,729,397 B2
(45) Date of Patent: Sep. 8, 2026

(54) IMMUNE REPERTOIRE PROFILING BY PRIMER EXTENSION TARGET ENRICHMENT

(71) Applicant: Roche Sequencing Solutions, Inc., Pleasanton, CA (US)

(72) Inventors: Jan Berka, Pleasanton, CA (US); Richard Dannebaum, Pleasant Hill, CA (US); Brian Godwin, Livermore, CA (US); Joseph Platzer, Oakland, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1210 days.

(21) Appl. No.: 17/753,937

(22) PCT Filed: Sep. 16, 2020

(86) PCT No.: PCT/EP2020/075853

§ 371 (c)(1),
(2) Date: Mar. 18, 2022

(87) PCT Pub. No.: WO2021/053008

PCT Pub. Date: Mar. 25, 2021

(65) Prior Publication Data

US 2022/0372566 A1 Nov. 24, 2022

Related U.S. Application Data

(60) Provisional application No. 62/903,224, filed on Sep. 20, 2019.

(51) Int. Cl.

*C12Q 1/6858* (2018.01)
*C12N 15/10* (2006.01)
*C12Q 1/6874* (2018.01)

(52) U.S. Cl.

CPC ....... *C12Q 1/6858* (2013.01); *C12N 15/1065* (2013.01); *C12Q 1/6874* (2013.01); *C12Q 2600/156* (2013.01)

(58) Field of Classification Search

CPC .............. C12N 15/1065; C12Q 1/6858; C12Q 2537/159

See application file for complete search history.

(56) References Cited

U.S. PATENT DOCUMENTS 12,264,315 B2 * 4/2025 Burgess ............... C12Q 1/6876
2013/0303461 A1 11/2013 Iafrate et al.

(Continued)

FOREIGN PATENT DOCUMENTS

WO WO-2017177308 A1 * 10/2017 ............ C40B 30/04
WO 2019/046817 A1 3/2019
WO 2019/121842 A1 6/2019

OTHER PUBLICATIONS

Jensen et al., "Kinetics for Hybridization of Peptide Nucleic Acids (PNA) with DNA and RNA, Studied with the BIAcore Technique," Biochemistry, vol. 36, No. 16, pp. 5072-5077. (Year: 1997).*

(Continued)

*Primary Examiner* — Young J Kim

(74) *Attorney, Agent, or Firm* — Charney IP Law LLC; Thomas M. Finetti

(57) ABSTRACT

The invention is a method of assessing a mammalian immune repertoire by primer extension target enrichment (PETE). Methods and compositions for assessing an immune repertoire and the status of additional genetic markers are disclosed.

13 Claims, 7 Drawing Sheets

Specification includes a Sequence Listing.

(56) References Cited

U.S. PATENT DOCUMENTS

| | | | | |
|---|---|---|---|---|
| 2017/0335386 | A1* | 11/2017 | Livingston ......... | C07K 14/7051 |
| 2018/0016630 | A1 | 1/2018 | Godwin et al. | |
| 2019/0017113 | A1 | 1/2019 | Corioni et al. | |
| 2022/0259659 | A1* | 8/2022 | Raymond ............ | C12Q 1/6883 |

OTHER PUBLICATIONS

Yang et al., "Identification and characterization of novel fusion genes in prostate cancer by targeted RNA capture and next-generation sequencing," Acta Biochim Biophys Sin, vol. 50, No. 11, pp. 1166-1172. (Year: 2018).*

International Searching Authority, International Search Report for International Patent Application No. PCT/EP2020/075853 (Mar. 25, 2021).

International Searching Authority, Written Opinion of the International Searching Authority for International Patent Application No. PCT/EP2020/075853 (Mar. 25, 2021).

* cited by examiner

Universal Adapter
J
D
V
Universal Adapter
J Release Primer Hybridization
cap
Solid support
Universal Adapter
J
D
V
Universal Adapter
J Release Primer Extension
cap
Solid support
Target molecule is specifically released for collection J
D
V
Universal Adapter
cap
V Capture Primer Extension
Capture extension products
Wash away all non-captured fragments
J
D
V
Universal Adapter
cap
Solid support

IMMUNE REPERTOIRE PROFILING BY PRIMER EXTENSION TARGET ENRICHMENT

CROSS REFERENCE TO RELATED APPLICATIONS

This patent application is a U.S. national stage patent application of International Patent Application No. PCT/EP2020/075853, filed Sep. 16, 2020, which claims priority from U.S. Provisional Patent Application No. 62/903,224, filed Sep. 20, 2019, both of which are incorporated herein by reference in their entireties.

SEQUENCE LISTING

The instant patent application contains a Sequence Listing, which has been submitted electronically in ASCII format and is hereby incorporated by reference in its entirety. The ASCII copy, created Sep. 16, 2020, is named "35716-WO_Sequence_Listing," and is 14,200 bytes in size.

FIELD OF THE INVENTION

The invention relates generally to enrichment of nucleic acid targets in a sample and more particularly, to enrichment of somatically rearranged nucleic acid targets including immune sequences, for downstream nucleic acid sequencing.

BACKGROUND OF THE INVENTION

Immune repertoire profiling (detecting all of the immunoglobulin and T-cell receptor sequences in an organism) has become a powerful tool to study basics of immunology and disease states, such as autoimmune disorders, cancer, infection, as well as organ transplantation. Sample preparation for simultaneous unbiased amplification of rearranged immune loci has proven challenging due to the enormous diversity of immune repertoires. For example, for T-cell receptors (TCR), repertoire diversity is established by somatic recombination of many genes (60 TCRB-V, 2 TCRB-D and 13 TCRB-J genes) and further through non-templated deletions and insertions of nucleotides at the V-D-J junctions. In case of immunoglobulins, an additional layer of diversity is provided by somatic hypermutation. Moreover, only one chromosome is typically rearranged in B and T cells, thus reducing the target copy number from 2 to 1 per cell genome.

Hybridization sequence capture methods have been described in relation to immune sequence profiling. However, these approaches suffer from low on-target yields due to many random or non-rearranged genomic DNA fragments not containing the whole V(D)J domain being pulled down, see Linnemann, C., et al., *High-throughput identification of antigen-specific TCRs by TCR gene capture*. Nat Med, 2013. 19(11): p. 1534-1541. Thus state of the art gene capture methods for immune repertoire profiling are only compatible with ultra-high throughput sequencers capable of detecting the targets in the presence of large volumes of background sequences. There is an unmet need for a method of target capture for immune profiling that has a high on-target yield.

Immune sequences are only one example of sequences that undergo somatic rearrangement or a change. Other sequences of clinical interest undergo somatic rearrangement: fusions in genes ALK, RET, ROS, ABL, MYC, NTRK1 and 3 and others are characteristic of certain cancers and can be used for diagnosis and monitoring of the disease, see Mitelman et al. (2007) *The impact of translocations and gene fusions on cancer causation*, Nat. Rev. Cancer 7:233-245.

Another example of sequences rearranged only in certain cells are messenger RNAs with alternative splicing. Up to 10% of annotated mutations in the Human Gene Mutation Database affect splicing sites, see Garcia-Blanco, et al., (2004) *Alternative splicing in disease and therapy*, Nature Biotech., 22, 535-546. Examples of alternatively spliced transcripts that are characteristic of disease include FGFR2 in prostate cancer, SMN (product of the SMN2 gene) in spinal muscular atrophy (SMA), beta-globin in beta-thalassemia and Factor IX in hemophilia. In case of SMA, some forms of treatment involve generating a functional splice variant in affected cells. Detecting these transcripts in the background of other splice variants can be used to diagnose disease and monitor treatment.

There is an unmet need more generally for an enrichment method that could enable capture and sequencing of a variety of somatically rearranged sequences from samples comprising a large background of non-rearranged germline sequences.

SUMMARY OF THE INVENTION

The invention comprises a method of determining an immune profile from a library of nucleic acids. Specifically, the immune profile is determined by primer extension target enrichment where a plurality of target-specific barcoded primers is used to capture rearranged immune sequences. Other (or additional) rearranged somatic sequences and other sequences of interest can be captured by the claimed method.

In one embodiment, the invention is a method for enrichment of at least one target nucleic acid containing a rearranged immune sequence having a V gene, a D gene and a J gene the method comprising: providing a library of nucleic acids having at least one adaptor; hybridizing a first oligonucleotide comprising a sequence complementary to the V gene and further comprising a capture moiety to a rearranged immune sequence in a library of nucleic acids; extending the hybridized first oligonucleotide with a first polymerase, thereby producing a first primer extension complex comprising the target nucleic acid and the extended first oligonucleotide; capturing the first primer extension complex via the capture moiety of the first oligonucleotide; hybridizing a second oligonudeotide comprising a sequence complementary to the J gene to the rearranged immune sequence in the captured first primer extension complex; extending the hybridized second oligonudeotide with a second polymerase, thereby producing a second primer extension complex comprising the target nucleic acid and the extended second oligonucleotide, thereby liberating the extended first oligonucleotide; wherein the target nucleic acid within the second primer extension complex is enriched relative to the initial library of nucleic acids. The method may further comprise amplifying the target nucleic acid, e.g. by exponential or linear method. The method may further comprise sequencing the target nucleic acid. The second polymerase may have a strand displacement activity.

In some embodiments, the capture moiety of the first oligonucleotide is selected from a capture sequence, a chemical moiety for which a ligand is available or an antigen for which an antibody is available, or wherein the capture moiety is a capture sequence complementary to a capture oligonucleotide which comprises a modified nucleotide increasing the melting temperature of the capture oligonucleotide, e.g., 5-methyl cytosine, 2,6-diaminopurine, 5-hydroxybutyl-2'-deoxyuridine, 8-aza-7-deazaguanosine, a ribonucleotide, a 2'O-methyl ribonucleotide and locked nucleic acid.

In some embodiments, the first oligonucleotide is bound to a solid support via the capture moiety prior to hybridizing the first oligonucleotide to the target nucleic acid.

In some embodiments, the adaptor comprises at least one barcode.

In some embodiments, the first oligonucleotide complementary to a V-gene is selected from sequences listed in Table 1 and the second oligonucleotide complementary to a J-gene is selected from sequences listed in Table 2.

In some embodiments, the nucleic acids in the library have a single adaptor having a first amplification primer binding site and the release primer comprises a second amplification primer binding site. In some embodiments, the nucleic acids in the library have two adaptors, each having an amplification primer binding site.

In some embodiments, the invention is a method of assessing the status of a patient's immune system by determining the rearranged immune sequences according to the method of claim 1 and further determining the expression of T-cell markers selected from: markers of T-cell type, markers of T-cell exhaustion, markers of T-cell activation, markers of tissue-resident memory cells, and markers of tumor-reactive T-cells. Examples of markers are CD45, CD3, CD8, CD39, CD25, IL-7R, CD4, CXCR3, CCR6, CD3G, CD3D, CD3E, CD2, CD8A, GZMA FOXP3, CD19, CD79A, PDCD1, HAVCR2, IFNG, TNF, ITGAE and CXCR6.

In some embodiments, the invention is a method of assessing the status of a patient by determining the rearranged immune sequences according to the method of claim 1 and further determining expression of one or more sequences listed in Table 3 (a), 3(b) or 3(c).

In some embodiments, the invention is a kit for enrichment of at least one target nucleic acid containing a rearranged immune sequence having a V gene, a D gene and a J gene, the kit comprising: a first oligonucleotide complementary to a V gene and comprising a capture moiety; a second oligonucleotide complementary to a J gene; a first amplification primer; and a second amplification primer, wherein the first oligonucleotide comprises a capture moiety. The capture moiety in the first oligonucleotide may be a capture sequence at least partially complementary to a capture oligonucleotide, the kit further comprising the capture oligonucleotide.

In some embodiments, the invention is a composition, comprising: a library of nucleic acids comprising at least one target nucleic acid containing a rearranged immune sequence having a V gene, a D gene and a J gene, each of the nucleic acids in the library having at least one adapter, an extended first oligonucleotide including at least one capture moiety hybridized to the V gene in the target nucleic acid, a solid support bound to the at least one capture moiety; a second oligonucleotide hybridized to the J gene; and a polymerase associated with a 3' end of the second oligonucleotide.

In some embodiments, the invention is a method for enrichment of at least one target nucleic acid containing a gene fusion sequence comprising the first and the second fusion partner sequence the method comprising: providing a library of nucleic acids having at least one adaptor; hybridizing a first oligonucleotide comprising a sequence complementary to the first fusion partner and further comprising a capture moiety to a fusion sequence in a library of nucleic acids; extending the hybridized first oligonucleotide with a first polymerase, thereby producing a first primer extension complex comprising the target nucleic acid and the extended first oligonucleotide; capturing the first primer extension complex via the capture moiety of the first oligonudeotide; hybridizing a second oligonudeotide comprising a sequence complementary to the second fusion partner sequence in the captured first primer extension complex; extending the hybridized second oligonudeotide with a second polymerase, thereby producing a second primer extension complex comprising the target nucleic acid and the extended second oligonucleotide, thereby liberating the extended first oligonucleotide; and amplifying the target nucleic acid thereby enriching the target nucleic acid.

In some embodiments, the invention is a method for enrichment of at least one target nucleic acid containing a spliced transcript having a splice site, the method comprising: providing a library of nucleic acids having at least one adaptor; hybridizing a first oligonucleotide comprising a sequence complementary to a sequence 3'-of the splice site and further comprising a capture moiety to a fusion sequence in a library of nucleic acids; extending the hybridized first oligonucleotide with a first polymerase, thereby producing a first primer extension complex comprising the target nucleic acid and the extended first oligonucleotide; capturing the first primer extension complex via the capture moiety of the first oligonucleotide; hybridizing a second oligonucleotide comprising a sequence complementary to a sequence 5'-of the splice site in the captured first primer extension complex; extending the hybridized second oligonucleotide with a second polymerase, thereby producing a second primer extension complex comprising the target nucleic acid and the extended second oligonucleotide, thereby liberating the extended first oligonucleotide; and amplifying the target nucleic acid thereby enriching the target nucleic acid.

DETAILED DESCRIPTION OF THE INVENTION

Definitions

Figure 1:
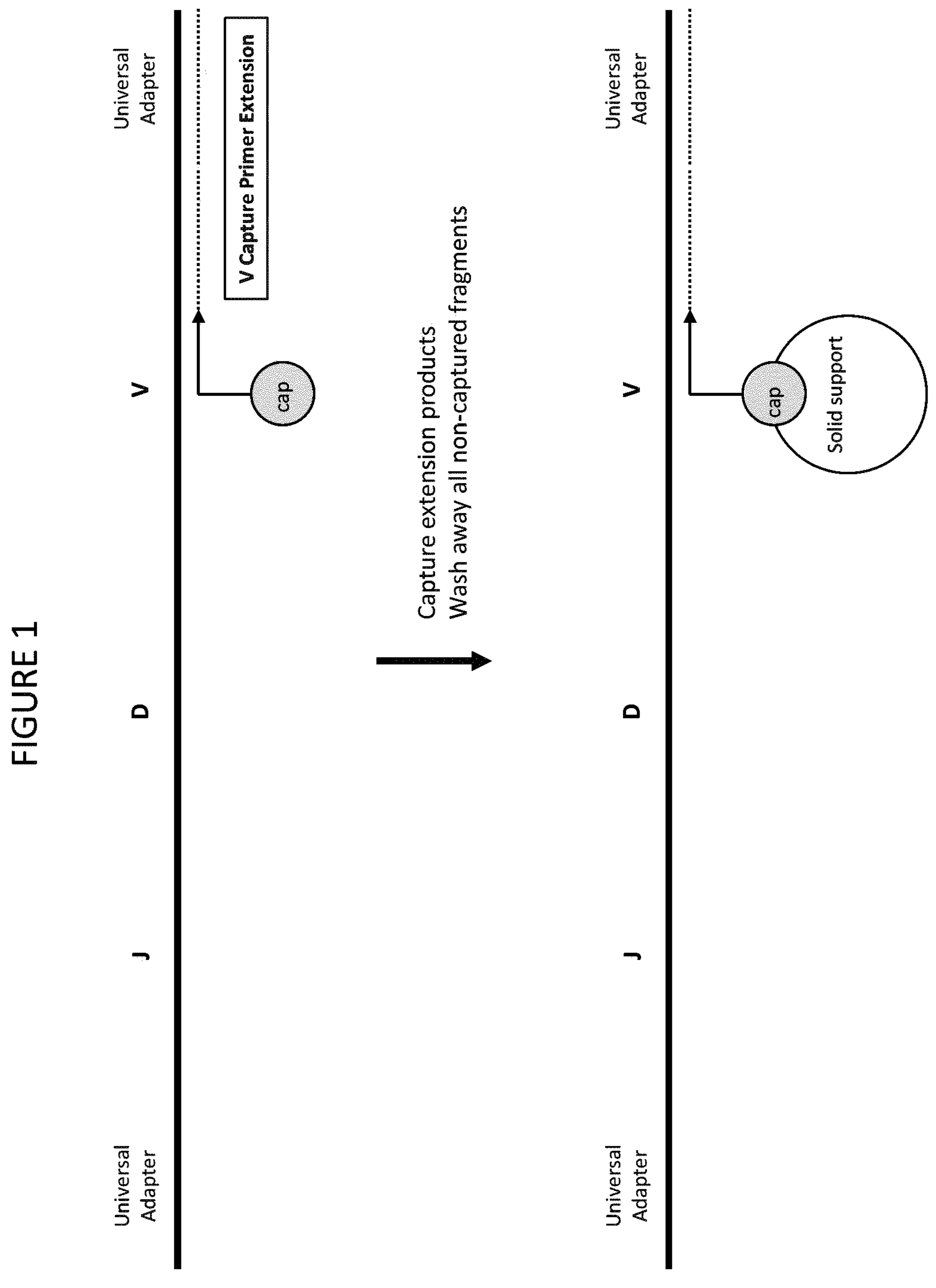
FIG. 1 is a diagram of the initial steps in one embodiment of the workflow.

The following definitions aid in understanding of this disclosure.

The term "adaptor" (or "adapter") refers to a nucleotide sequence that may be added to another sequence so as to import additional properties to that sequence. An adaptor can be single- or double-stranded, or may have both a single-stranded portion and a double-stranded portion.

The term "barcode" means a nucleotide sequence conferring identity to a molecule or a group of molecules sharing a common property or origin. A barcode may confer a unique identity to an individual molecule (and its copies). Such a barcode is a unique ID (UID). A barcode may confer an identity to an entire population of molecules (and their copies) coming from the same source (e.g., a sample). Such a barcode is a multiplex ID (MID) or sample ID (SID).

The term "clonotype" means a T-cell receptor (TCR) or an immunoglobulin (Ig) having a uniquely rearranged CDR3 sequence. The term includes both nucleic acid and protein versions of the sequence.

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The term "DNA polymerase" refers to an enzyme that performs template-directed synthesis of polynucleotides from deoxyribonucleotides. DNA polymerases include prokaryotic Pol I, Pol II, Pol III, Pol IV and Pol V, eukaryotic DNA polymerase, archaeal DNA polymerase, telomerase and reverse transcriptase. The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. In some embodiments, the following thermostable polymerases can be used: *Thermococcus litoralis* (Vent, GenBank: AAA72101), *Pyrococcus furiosus* (Pfu, GenBank: D12983, BAA02362), *Pyrococcus woesii, Pyrococcus* GB-D (Deep Vent, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025) and other archaeal B polymerases, such as GenBank AAC62712, P956901, BAAA07579)), thermophilic bacteria *Thermus* species (e.g., *flavus, ruber, thermophilus, lacteus, rubens, aquaticus*), *Bacillus stearothermophilus, Thermotoga maritima, Methanothermus fervidus*, KOD polymerase, TNA1 polymerase, *Thermococcus* sp. 9 degrees N-7, T4, T7, phi29, *Pyrococcus furiosus, P. abyssi, T. gorgonarius, T. litoralis, T. zilligii, T.* sp. GT, *P.* sp. GB-D, KOD, Pfu, *T. gorgonarius, T. zilligii, T. litoralis* and *Thermococcus* sp. 9N-7 polymerases. In some cases, the nucleic acid (e.g., DNA or RNA) polymerase may be a modified naturally occurring Type A polymerase. A further embodiment of the invention generally relates to a method wherein a modified Type A polymerase, e.g., in a primer extension, end-modification (e.g., terminal transferase, degradation, or polishing), or amplification reaction, may be selected from any species of the genus *Meiothermus, Thermotoga*, or *Thermomicrobium*. Another embodiment of the invention generally pertains to a method wherein the polymerase, e.g., in a primer extension, end-modification (e.g., terminal transferase, degradation or polishing), or amplification reaction, may be isolated from any of *Thermus aquaticus* (Taq), *Thermus thermophilus, Thermus caldophilus*, or *Thermus filiformis*. A further embodiment of the invention generally encompasses a method wherein the modified Type A polymerase, e.g., in a primer extension, end-modification (e.g., terminal transferase, degradation, or polishing), or amplification reaction, may be isolated from *Bacillus stearothermophilus, Sphaerobacter thermophilus, Dictoglomus thermophilum*, or *Escherichia coli*. In another embodiment, the invention generally relates to a method wherein the modified Type A polymerase, e.g., in a primer extension, end-modification (e.g., terminal transferase, degradation, or polishing), or amplification reaction, may be a mutant Taq-E507K polymerase. Another embodiment of the invention generally pertains to a method wherein a thermostable polymerase may be used to effect amplification of the target nucleic acid.

The terms "polynucleotide" and "oligonucleotide" are used interchangeably. Polynucleotide is a single-stranded or a double-stranded nucleic acid. Oligonucleotide is a term sometimes used to describe a shorter polynucleotide. An oligonucleotide may be comprised of at least 6 nucleotides or about 15-30 nucleotides. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191.

The term "primer" refers to a single-stranded oligonucleotide which hybridizes with a sequence in the target nucleic acid and is capable of acting as a point of initiation of synthesis along a complementary strand of nucleic acid under conditions suitable for such synthesis. The primer may be partially or perfectly complementary to the target nucleic acid as long as it can form a stable hybrid with the target and be extended by a nucleic acid polymerase. The term "forward and reverse primers" refers to a pair of primers complementary and to opposite strands of the target nucleic acids at sites flanking the target sequence. Forward and reverse primers are capable of exponentially amplifying the target by polymerase chain reaction (PCR).

The term "probe" refers to a single-stranded oligonucleotide (or a double-stranded oligonucleotide which is denatured into signal strands prior to use) which hybridizes with a sequence in the target nucleic acid and is capable of forming a stable hybrid with the target. The probe may be partially or perfectly complementary to the target nucleic acid as long as it can form a stable hybrid with the target under the hybridization conditions.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA). In some embodiments, as will be clear to one skilled in the art from context, the term "sample" refers to a preparation that is obtained by processing (e.g., by removing or adding one or more components) a primary sample obtained from a patient. For example, such processing may include removing some tissue material (including blood components) from the sample and lysing any intact cells to release nucleic acids.

The term "sequencing" refers to any method of determining the sequence of nucleotides in the target nucleic acid.

The term "solid support" refers to any solid material capable of interacting with a capture moiety. A solid support can be a solution-phase support capable of suspension in a solution (e. g., a glass bead, a magnetic bead, or another like particle), or a solid-phase support (e.g., a silicon wafer, a glass slide, or the like). Examples of solution-phase supports include superparamagnetic spherical polymer particles such as DYNABEADS magnetic beads or Beckman Coulter AMPure solid phase reversible immobilization (SPRI) paramagnetic beads (ThermoFisher Scientific, Waltham, Mass.) or magnetic glass particles such as described in U.S. Pat. Nos. 6,274,386, 7,371,830, 6,870,047, 6,255,477, 6,746,874 and 6,258,531.

The terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "universal primer" and "universal priming site" refer to a primer and priming site not naturally present in the target sequence. Typically, the universal priming site is present in adapters or target-specific primers. The universal primer can bind to and direct primer extension from the universal priming site.

The mammalian immune system relies on somatic gene rearrangements to form a repertoire of T- and B-cell antigen receptors. The T-cell antigen receptor (TCR) consists of one of two heterodimers: a heterodimer of an alpha chain encoded by TCRA locus and a beta chain encoded by TCRB locus, or a heterodimer of a delta chain encoded by TCRD locus and gamma chain encoded by TCRG locus. In lymphoid cells the TCR genes undergo rearrangement to generate a repertoire of TCR sequences. The TCR and immunoglobulin loci include variable (V), diversity (D), joining (J) gene segments, and constant (C) genes. The TCRA locus (chromosome 14) consists of 70-80 $V_\alpha$ gene segments, each having a leader sequence (L), 61 $J_\alpha$ gene segments and a single C gene. The TCRB locus (chromosome 7) consists of 52 functional $V_\beta$ gene segments, a single D gene segment, 6-7 J gene segments and a single C gene. The TCRD locus is located between the J and V gene segments of the TCRA locus. The immunoglobulin genes are organized into three loci: two light chain (kappa and lambda) and heavy chain loci. The lambda light chain locus (chromosome 22) includes a cluster of $V_\lambda$ gene segments, four sets of $J_\lambda$ gene segments each linked to a single $C_\lambda$ gene. In the kappa light chain locus (chromosome 2), the cluster of $V_\kappa$ gene segments is followed by a cluster of $J_\kappa$ gene segments, and then by a single $C_\kappa$ gene. The heavy chain locus (chromosome 14) has separate dusters of $V_H$, $D_H$, and $J_H$ gene segments and CH genes. The heavy chain locus contains a series of C regions corresponding to different immunoglobulin isotypes.

Most T cells have one of each productively rearranged TCRA and TCRB (or two rearranged TCRG and TCRD). Most B cells have one of each productively rearranged Ig heavy-chain and light-chain gene (either IGK or IGL).

Each TCR contains complementarity determining regions (CDRs), framework regions (FRs) and a constant region. The diversity of TCRs is determined by the third complementarity-determining region (CDR3) loops of the variable domain in the alpha and beta chains. The diversity is generated by selecting and combining each of the V, D and J segments and further by in-del alterations at the segment junctions during the somatic rearrangement process.

In immunoglobulins (Ig), both H and L chains contain complementarity determining regions (CDR) involved in antigen recognition, and a constant domain. Diversity of Ig is determined by the hypervariable complementarity determining regions (CDR) created by the combinatorial joining of the $V_H$, $D_H$, and $J_H$ gene segments and by in-del alterations at the segment junctions. Ig sequence diversity is further augmented by somatic hypermutation (SHM) throughout the rearranged gene. SHM occurs in CDR1, CDR2 and CDR3 regions. See *Immunobiology: The Immune System in Health and Disease.* 5th edition, Janeway C. A. Jr, Travers P, Walport M, et al., New York: Garland Science; 2001.

Genomic sequencing of rearranged TCR or Ig genes (donotypes) involves isolating and amplifying these gene sequences from immune cells. To date, the state of the art methods of assessing immune repertoire relied on multiplex PCR amplification prior to sequencing the amplified libraries of immune sequences (See US20170335386, US20170335386, and U.S. Pat. No. 9,809,813). Any multiplex reaction (e.g., amplification or sequencing) is associated with sequence bias, i.e., unequal efficiency of amplification (or sequencing) resulting in underrepresentation (or even loss) of come sequences and overrepresentation of others. Primer Extension Target Enrichment (PETE) (See e.g., US20170037459A1, US20180023131, US20180087108 and WO2019121842.

Primer Extension Target Enrichment (PETE) is a method of selectively amplifying target nucleic acids with reduced bias. The instant invention is a method of determining immune repertoire by unidirectional dual primer extension method.

This invention describes a method for targeted enrichment of rearranged immune sequences including T-cell immune receptor loci (TCR alpha, beta, gamma, delta) and Immunoglobulin loci from human genomic DNA or cDNA prepared from mRNA. The method is not limited to human TCRs, it could, in principle, be applied to any organism for which TCR sequences are known, and also to immunoglobulin loci. In one embodiment, the method captures TCR repertoire and establishes clonal structure of TCR CDR3.

The method of the invention is not limited to rearranged immune sequences. In some embodiments, the method is applied to other somatic gene rearrangements including gene fusions and alternatively spliced RNA transcripts.

NGS profiling of BCR and TCR repertoires has become a powerful tool to study basics of immunology and disease states, such as autoimmune disorders, cancer, infection, as well as organ transplants. Sample preparation for unbiased amplification of rearranged immune loci has proven challenging due to the enormous diversity of immune repertoires. Repertoire diversity is established by somatic recombination of many genes (e.g. 60 TCRB-V, 2 TCRB-D and 13 TCRB-J genes). The diversity is further augmented by non-templated deletions and insertions of nucleotides at the V-D-J junctions, and in case of immunoglobulin receptors, somatic hypermutation. Moreover, only one chromosome is typically rearranged in B and T cells, thus reducing the target gene copy number from 2 to 1 per cell genome.

Hybridization sequence capture methods have been described, but these approaches suffer from low on-target yields due to many random genomic DNA fragments not containing the whole V(D)J domain being pulled down. Thus typical gene capture methods for immune repertoire profiling are only compatible with ultra-high throughput sequencers. The cost of sequencing the captured non-immune sequences is a substantial burden.

The instant invention is based on a novel dual primer extension technology (see WO2019121842) that first enriches for selected targets by binding and extending a target-specific primer ("capture primer") and capturing the extension complex, followed by washing away of non-bound targets, and then followed by a selective release (or displacement) of the first primer extension product by a second target-specific primer ("release primer") extension. The targets present in the second primer extension complex are collected for optional amplification and further analysis. By pairing V primers with J primers (e.g., V capture primers with J release primers) (FIGS. 1-6) the instant method enables selective capture and enrichment of rearranged immune sequences such as TCRs and BCRs.

In one embodiment, (FIGS. 1-3) the adaptors on the original nucleic acid molecule contain universal primer sites for amplification of the enriched targets. In another embodiment, (FIGS. 4-6) the release primer contains a universal primer site to be paired with the universal primer binding site in the 3'-adaptor. Sequences upstream, downstream, or in between the capture primer and the release primer can be enriched for and analysed by this method.

A sample used in the method of the invention comprises any individual (e.g., non-human mammal, human, or patient). The nucleic acids can be extracted from the sample, or the sample can be directly subjected to the methods of the invention. The starting sample can also be extracted or isolated nucleic acids, DNA or RNA. The sample can constitute any tissue or fluid obtained from an organism. For example, the sample may be an organ (e.g., lymph node) or tumor biopsy or a blood or plasma sample. In some embodiments, the sample is a formalin-fixed, paraffin-embedded (FFPE) sample.

Methods of DNA extraction are well-known in the art. See J. Sambrook et al., "Molecular Cloning: A Laboratory Manual," 1989, 2nd Ed., Cold Spring Harbor Laboratory Press: New York, N.Y.). A variety of kits are commercially available for extracting nucleic acids (DNA or RNA) from biological samples (e.g., BD Biosciences Clontech (Palo Alto, Cal.), Epicentre Technologies (Madison, Wisc.); Gentra Systems, INC. (Minneapolis, Minn.); and Qiagen, INC. (Valencia, Cal.), Ambion, Inc. (Austin, Tex.); BioRad Laboratories (Hercules, Cal.); and more.

In some embodiments, the nucleic acid from the sample is first converted into a library of adapted nucleic acids. In some embodiments, the library is a whole genome library, a whole exome library or a transcriptome library. Methods of library preparation are known in the art and commercial products exists for library preparation, see e.g., KAPA library preparation kits (Kapa Biosystems, Wilmington, Mass.), including Hyper Prep, HyperPlus and HTP/LTP library preparation kits. A suitable library preparation method yields an even representation of nucleic acids from the original sample, wherein each nucleic acids is of uniform size and optionally, comprises an adaptor on one or both ends. The libraries may be enriched for certain sequences or be depleted of certain sequences (e.g., repetitive sequences or the like).

In some embodiments, DNA and RNA are isolated and analyzed simultaneously. Protocols for simultaneous DNA and RNA isolation and processing by primer extension target enrichment (PETE) have been disclosed, see e.g., WO2018/162538 and U.S. Provisional Application Ser. No. 62/888,963 "Single-tube preparation of DNA and RNA for sequencing" filed on Aug. 19, 2019.

The primers used in the instant method comprise a target specific sequence. Preferably, the target specific sequence is located in the 3'-ortion of the primer. In addition to the target-specific region, the primer may comprise additional sequences. Preferably, these sequences are located to the 5'-end of the target-specific region. In other embodiments, it may be possible to include these sequences elsewhere within the primer as long as the target-specific region is capable of hybridizing to the target and driving the primer extension reaction as described below. The additional sequences within the primer may include one or more barcode sequences, such as a unique molecular identification sequence (UID) or a multiplex sample identification sequence (MID). The barcode sequences may be present as a single sequence or as two or more sequences.

In some embodiments, the additional sequences include sequences that facilitate ligation to the 5'-end of the primer. The primer may contain a universal ligation sequence that enables ligation of an adapter as described in the following section.

In some embodiments, the additional sequences include one or more a binding sites for one or more universal amplification primers.

In some embodiments, the primer comprises a universal capture sequence that enables capture of the primer and primer extension products via hybridization to a capture oligonucleotide.

The distance between the primers can 0, 1, 10, 100 or even 1000 bases long. By pairing V primers with J primers (ex. V capture primers with J release primers) and employing this dual primer technology on typical fragmented libraries, it is possible to selectively capture rearranged sequences present in genomic DNA. Non-rearranged V and J genomic segments would be too far apart (10,000 or more bases) to be on the same short library fragment (100s of bases) and therefore not enriched.

A large number of immune receptor and TCR V, D and J region gene sequences, in non-rearranged and productively rearranged genomic DNA are known. Sequences of TCR and Ig have been published. See, e.g., US20170335386, US20170335386, and U.S. Pat. No. 9,809,813. These and other similar sources may be used to design and manufacture the gene-specific primers used in the present invention.

In some embodiments, the sequences of capture primers shown in Table 1 are used. In some embodiments, the capture primers are biotinylated as shown in Table 1. In some embodiments, the release primers shown in Table 2 are used.

TABLE 1

V gene-specific capture primers (SEQ ID No: 1-63)

| Well Position | Sequence |
|---|---|
| A1 | /5Bio/TATAAGCGAGAGCTGTCAGGGCATTC |
| B1 | /5Bio/CAACTGAGAATTGATCATCGAATATTTCAGACTTCTCTGAG |
| C1 | /5Bio/CTTTGTCTGGAGATTTAGGTGAGAATCGATTTGG |
| D1 | /5Bio/CTTTGTCTGGAGATTTAGGTGAGAAGCGATTTGG |
| E1 | /5Bio/ATGAGCTTTGTCTGGAGAGTCAGGTG |
| F1 | /5Bio/ATGAACTTTGTCTGGAGAGTCAGGTG |
| G1 | /5Bio/GAGAGCTGTTGGGGCATTCAGG |
| H1 | /5Bio/TAGAGAACTGGCGCCCTGAGAATC |
| A2 | /5Bio/TATGGACGTGGTGAGCTGAGAATCAATTAGG |
| B2 | /5Bio/CATGGAACTGGCGCCCTGA |
| C2 | /5Bio/TAGGGAACTGGAGACCTGAGAATCTAGGA |
| D2 | /5Bio/GCTGAGAATCGATCAGGGAAGTTTCCTC |
| E2 | /5Bio/TGACCTGAGAATCGATCAGGGAAGTTG |
| F2 | /5Bio/TGACCTGAGAATTGATCAGGGAAGTTTCCT |
| G2 | /5Bio/CGACCTGAAAATCTAGGAGGGAAGTTTCC |
| H2 | /5Bio/AATCTGGAGACATTGTAGCCATTGGGG |
| A3 | /5Bio/TTGTAGCCATCAGGGACCTCTCC |
| B3 | /5Bio/GCTCTGGAGACACTATAACCATCAGGGA |
| C3 | /5Bio/GACATTGTAGCCATTGGGGACTTCTCC |
| D3 | /5Bio/TTGTAGCCATTCGGGACTTCTCCTTT |
| E3 | /5Bio/GATCTGGAGACATTGTAGCCATTGGGAAC |
| F3 | /5Bio/AATCTAGAGACATTGTAGCCATTGGGGACTTC |
| G3 | /5Bio/TACATTGTAGCCATCGGGGACTTCTC |
| H3 | /5Bio/ACCTCTGTGCAGAGAACCGATCAC |
| A4 | /5Bio/CCAGTCCTCTCTGCAGAGAAGCG |
| B4 | /5Bio/TCAGGCCTGACTGCAAAGAACC |
| C4 | /5Bio/CTCTGCAGAGAACCGACCACTG |
| D4 | /5Bio/ACCTCTCTGTGGAGAATTGATCACTGAGC |
| E4 | /5Bio/CCTCAGGCCTCTCTGCAGAGAA |
| F4 | /5Bio/TTTCTGCAAAGAAGCGATCACTGGG |
| G4 | /5Bio/AGATCCCTTAGGCCTCTCTGCAG |
| H4 | /5Bio/CTTGAGCTTGTTTCCAGAGACATTGTACCCTTC |
| A5 | /5Bio/CTCAAGCTTGTTTCAAGAAACACAGTACCCC |
| B5 | /5Bio/GTTTAGTTCAGAGTGCAAGTCAGGGAACTG |

TABLE 1-continued

| V gene-specific capture primers (SEQ ID No: 1-63) | |
|---|---|
| Well Position | Sequence |
| C5 | /5Bio/CTGTAGCCATCTGAGACTTCTCCTTTGTTAGT |
| D5 | /5Bio/TAGCCATCGGGGACTTCTCCTTTATCT |
| E5 | /5Bio/CTATAGCCATCTGAGACTTCTCCTTTGTCAGTATC |
| F5 | /5Bio/GAGCCTCTCTGCAGAAAATCGATCCTTAG |
| G5 | /5Bio/ACATCAGGCATCTGTGCTGAGAATCAA |
| H5 | /5Bio/CCATCAGGCCTCTCAGCTGAGAAT |
| A6 | /5Bio/GCATTAGGCATCTTAGCTGAGAATCGATCC |
| B6 | /5Bio/TAAAGTTGCATCAGGCATCTCTGCTGAG |
| C6 | /5Bio/ACTGAACTGTTGAGCTGAGAATCGATCAG |
| D6 | /5Bio/ATACGTCCCTCCAGTCCTTTCAGCTA |
| E6 | /5Bio/AGAAAGAAGTGTTCGGCCTCCTGG |
| F6 | /5Bio/AGGGTGAATTTGGGAGGCACTTAGC |
| G6 | /5Bio/ACGTTCCGTTAGGTCTTTCAGCTGTG |
| H6 | /5Bio/GGCCCTCTTTGGGAAATTCAGCAG |
| A7 | /5Bio/CCCGAGAGACGCTGTACCCT |
| B7 | /5Bio/TGTCAGAGTGGACAAGGTCAGGC |
| C7 | /5Bio/TGGAGCATTGGGCTAAAAATCGCTCAT |
| D7 | /5Bio/CTCTTGGCAGACACGTAGCCTTCA |
| E7 | /5Bio/GCGTTCTTGGGGCATTGAGATGAG |
| F7 | /5Bio/TGTCGAGAGACACTGTATCCATCAGAGATCT |
| G7 | /5Bio/TATTCTGGAGACTGTTGACTCAGAGGAAAGATCT |
| H7 | /5Bio/CATGATACCCCTCAGAGATATCTCCTTTTTCAGTG |
| A8 | /5BI0/CTTTTCGAGAGACTTTGTACCCTTCAGGAAC |
| B8 | /5Bio/TCTCTCTAGAGACACTGTACCCCTCAG |
| C8 | /5Bio/TTGAGAATGTTAGGTTTGGGCGGCT |
| D8 | /5Bio/TGAACTGCCGGTCCTGGG |
| E8 | /5Bio/TGCCAGGAAATATTTTCAATAGGGATATGTCTCTAATCAA |
| F8 | /5Bio/GTTAGAATGACTATGCTGACTCAGGGCATCT |
| G8 | /5Bio/CCTTCATAGACCAATTTAGAAG |

TABLE 2

| J-gene specific release primers (SEQ ID NO: 64-76) | |
|---|---|
| A11 | GTCTTACCTACAACTGTGAGTCTGGTGCC |
| B11 | CCTTACCTACAACGGTTAACCTGGTCCC |
| C11 | CTTACTCACCTACAACAGTGAGCCAACTTCC |
| D11 | ATACCCAAGACAGAGAGCTGGGTTCC |
| E11 | AACTTACCTAGGATGGAGAGTCGAGTCCC |
| F11 | CTGTCACAGTGAGCCTGGTCCC |
| G11 | CACGGTGAGCCGTGTCCC |
| H11 | CCAGTACGGTCAGCCTAGAGCC |
| A12 | CACTGTCAGCCGGGTGCC |
| B12 | CACTGAGAGCCGGGTCCC |
| C12 | ACCAGGAGCCGCGTGCC |
| D12 | CACGGTCAGCCTGCTGCC |
| E12 | GACCGTGAGCCTGGTGCC |

In some embodiments, in addition or instead of primers specific for rearrange immune sequences, primers specific to other genes are used. The primers from this method can be combined with other genomic or transcriptomic targets, generating an enrichment panel for applications including but not limited to identification of SNVs, InDels, CNVs, MSI, translocation events and/or fusion events.

In some embodiments, the additional target sequences are somatically rearranged sequences other than immune sequences. In some embodiments, the target sequences are fusion genes common in cancer. In some embodiments, the target sequences are selected from fusions of ALK, NTRK1, FGFR2, FGFR3, RET, ROS1 and FIP1L1-PDGFRA. In some embodiments, the target sequences are genes or transcribed sequences subject to alternative splicing.

In some embodiments, the additional target sequences are genes or biomarkers of interest, e.g., biomarkers of disease. In some embodiments, additional biomarkers are selected from Table 3 (a)-(c) below.

TABLE 3 (a)

| Additional genes detected by the method of the invention | | | |
|---|---|---|---|
| APC | ALK* | ERBB2 | NRAS |
| BRCA1 | BRAF | KRAS | PDGFRA |
| BRCA2 | DPYD | MET | ROS1* |
| EGFR | KIT | TP53 | UGT1A1 |
| RET | | | |

TABLE 3 (b)

| Additional genes detected by the method of the invention | | | | | |
|---|---|---|---|---|---|
| APC | KRAS | ABL1 | FGFR3 | JAK3 | RAF1 |
| BRCA1 | MET | AKT1 | FLT1 | KDR | RNF43 |
| BRCA2 | TP53 | AKT2 | FLT3 | MAP2K1 | TERTpromoter |
| EGFR | KIT | ARAF | FLT4 | MAP2K2 | TSC1 |
| ERBB2 | NRAS | CDK6 | GATA3 | MTOR | TSC2 |
| ALK | PDGFRA | CSF1R | GNA11 | NFE2L2 | PTEN |
| BRAF | RET | CTNNB1 | GNAQ | NTRK1 | RB1 |
| DPYD | ROS1 | DDR2 | GNAS | PDGFRB | SMAD4 |
| AR | MSH2 | EZH2 | IDH1 | PIK3CA | SMO |
| CCND1 | MSH6 | FGFR1 | IDH2 | PIK3R1 | STK11 |
| CCND2 | NF2 | FGFR2 | JAK2 | PTCH1 | VHL |
| CCND3 | PDCD1LG2 | CDK4 | ESR1 | KEAP1 | UGT1A1 |
| CD274 | PMS2 | CDKN2A | FBXW7 | MLH1 | |

TABLE 3 (c)

| Additional genes detected by the method of the invention | | | | | | |
|---|---|---|---|---|---|---|
| ABCC5 | CSMD1 | FAT1 | HTR1E | MAP7D3 | PIK3CA | SV2A |
| ABCG2 | CSMD3 | FBN2 | HTR2C | MKRN3 | PIK3CG | T |
| ACTN2 | CTNNB1 | FBXL7 | IFI16 | MMP16 | PKHD1L1 | THSD7A |
| ADAMTS12 | CTNND2 | FBXW7 | IL7R | MTX1 | POLE | TIAM1 |
| ADAMTS16 | CYBB | FCRL5 | INSL3 | MYH7 | POM121L12 | TMEM200A |
| ARFGEF1 | DCAF12L1 | FOXG1 | ITGA10 | MYT1L | PREX1 | TNFRSF21 |
| ASTN1 | DCAF12L2 | FRYL | ITSN1 | NAV3 | PTPLA | TNN |
| ASTN2 | DCAF4L2 | GBA3 | KCNA5 | NEUROD4 | RALYL | TNR |
| AVPR1A | DCLK1 | GBP7 | KCNB2 | NFE2L2 | RFX5 | TRHDE |
| BCHE | DCSTAMP | GJA8 | KCNC2 | NLGN4X | RIN3 | TRIM58 |
| BPIFB4 | DDI1 | GPR139 | KCNJ3 | NLRP3 | RNASE3 | TRPS1 |
| C6 | DLGAP2 | GRIA2 | KCTD8 | NMUR1 | ROBO2 | UGT3A2 |
| C6orf118 | DMD | GRIK3 | KEAP1 | NOL4 | SEMA5B | USH2A |
| CA10 | DNTTIP1 | GRIN2B | KIAA1211 | NPAP1 | SLC18A3 | USP29 |
| CACNA1E | DOCK3 | GRIN3B | KIF17 | NR0B1 | SLC39A12 | VPS13B |
| CDH12 | DSC3 | GRM1 | KIF19 | NRXN1 | SLC6A5 | WBSCR17 |
| CDH18 | DSCAM | GRM5 | KLHL31 | NXPH4 | SLC8A1 | WIPF1 |
| CDH8 | EGFLAM | GRM8 | KPRP | NYAP2 | SLITRK1 | WSCD2 |
| CDH9 | EPHA5 | GSX1 | LPPR4 | OPRD1 | SLITRK4 | ZC3H12A |
| CDKN2A | EPHA6 | HCN1 | LRFN5 | P2RY10 | SLITRK5 | ZFPM2 |
| CHRM2 | EYS | HCRTR2 | LRP1B | PAX6 | SLPI | ZIC1 |
| CNTN5 | FAM135B | HEBP1 | LRRC7 | PCDH15 | SMAD4 | ZIC4 |
| CNTNAP2 | FAM151A | HECW1 | LRRTM1 | PDYN | SOX9 | ZNF521 |
| CPXCR1 | FAM5B | HS3ST4 | LRRTM4 | PDZRN3 | SPTA1 | ZSCAN1 |
| CPZ | FAM5C | HS3ST5 | LTBP4 | PGK2 | ST6GALNAC3 | KIT |
| CRMP1 | FAM71B | HTR1A | MAP2 | PHACTR1 | STK11 | NRAS |
| APC | KRAS | ALK | PDGFRA | MET | BRAF | RET |
| BRCA1 | BRCA2 | TP53 | DPYD | EGFR | ERBB2 | UGT1A1 |

In some embodiments, additional target sequences are RNA transcripts or cDNA sequences of immune cell markers further characterizing the population of immune cells from which somatic rearranged immune sequences were obtained. The additional sequences are selected from markers of T-cell type, T-cell exhaustion, T-cell activation, markers of tissue-resident memory cell, markers and markers of tumor-reactive T-cells. The additional targets sequences may be transcripts of one or more of CD45, CD3, CD8, CD39, CD25, IL-7R, CD4, CXCR3, CCR6, CD3G, CD3D, CD3E, CD2, CD8A, GZMA FOXP3, CD19, CD79A, PDCD1, HAVCR2, IFNG, TNF, ITGAE, CXCR6, (see Yost et al. (2019) *Clonal replacement of tumor specific T-cells following PD-1 blockade*, Nature Medicine, doi.org/10.1038/s41591-019-0522-3. To facilitate the workflow of this embodiment, RNA and DNA may be isolated from the sample and processed simultaneously while the primer extension target enrichment (PETE) processes on DNA and RNA run in parallel as described e.g., in WO2018/162538 and U.S. Provisional Application Ser. No. 62/888,963 "Single-tube preparation of DNA and RNA for sequencing" filed on Aug. 19, 2019.

The primer extension step is performed by a nucleic acid polymerase. Depending on the type of nucleic acid being analysed, the polymerase may be a DNA-dependent DNA polymerase ("DNA polymerase") or an RNA-dependent DNA polymerase ("reverse transcriptase"). In some embodiments, the DNA polymerase is a Hot Start polymerase or a similar conditionally activated polymerase. For the amplification step, a thermostable DNA polymerase is used, for example polymerase is a Taq or Taq-derived polymerase (e.g., KAPA 2G polymerase from KAPA Biosystems, Wilmington, Mass.).

In some embodiments, the invention comprises a step of adaptor ligation. The adaptor may be ligated to the ends of a double stranded DNA molecule formed as described herein. Adaptors of various shapes and functions are known in the art (see e.g., PCT/EP2019/05515 filed on Feb. 28, 2019, U.S. Pat. Nos. 8,822,150 and 8,455,193)

The adaptor may be double-stranded, partially single stranded or single stranded. In some embodiments, a Y-shaped, a hairpin adaptor or a stem-loop adaptor is used wherein the double-stranded portion of the adaptor is ligated to the double stranded nucleic acid formed as described herein.

In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules or isolated non naturally-occurring molecules.

The adaptor further comprises a primer binding site for at least one universal primer.

The double-stranded or partially double-stranded adaptor oligonucleotide can have overhangs or blunt ends. In some embodiments, the double-stranded DNA formed by the method described herein comprises blunt ends to which a blunt-end ligation can be applied to ligate a blunt-ended adaptor. In other embodiments, the blunt ended DNA undergoes A-tailing where a single A nucleotide is added to the blunt ends to match an adaptor designed to have a single T nucleotide extending from the blunt end to facilitate ligation between the DNA and the adaptor. Commercially available kits for performing adaptor ligation include AVENIO ctDNA Library Prep Kit or KAPA HyperPrep and HyperPlus kits (Roche Sequencing Solutions, Pleasanton, CA.). In some embodiments, the adaptor ligated (adapted) DNA may be separated from excess adaptors and unligated DNA.

In one aspect, a universal blocking oligonucleotide includes a nonspecific region flanked by first and second specific regions. The nonspecific region includes, for example, a run of inosines that align with the sample index sequence when the universal blocking oligonucleotide is hybridized to the target adapter sequence. The specific regions of the universal blocking oligonucleotide are complementary to the invariant portion of the adapter sequence and include one or more melting temperature ($T_m$) modified bases to increase the T. of the blocking oligonucleotide-adapter duplex. Examples of $T_m$-modified base substitutes are illustrated in Table 1.

TABLE 4

| Standard NTP | $T_m$-modified substitute base |
|---|---|
| ATP | 8-aza-7-Br-7-deaza-2,6-diaminopurine |
| CTP | 5-propynyl-dC |
| GTP | 8-aza-7-Br-7-deaza-dG |
| TTP | 5-propynyl-dU |

In another aspect, unamplified nucleic acid libraries prepared with two different adapter sequences could be processed without blocking oligonucleotides if the adapter ends do not hybridize to one another. Adapter types suitable for this approach include forked and Y-shaped adapters.

Analysing individual molecules typically requires molecular barcodes such as described in U.S. Pat. Nos. 7,393,665, 8,168,385, 8,481,292, 8,685,678, and 8,722,368. A unique molecular barcode is a short artificial sequence added to each molecule in the patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy (Newman, A., et al., (2014) *An ultrasensitive method for quantitating circulating tumor DNA with broad patient coverage*, Nature Medicine doi:10.1038/nm.3519).

Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample (Newman, A., et al., (2016) *Integrated digital error suppression for improved detection of circulating tumor DNA*, Nature Biotechnology 34:547).

In some embodiments of the invention, the adaptor comprises one or more barcodes. A barcode can be a multiplex sample ID (MID) used to identify the source of the sample where samples are mixed (multiplexed). The barcode may also serve as a unique molecular ID (UID) used to identify each original molecule and its progeny. The barcode may also be a combination of a UID and an MID. In some embodiments, a single barcode is used as both UID and MID. In some embodiments, each barcode comprises a predefined sequence. In other embodiments, the barcode comprises a random sequence. In some embodiments of the invention, the barcodes are between about 4-20 bases long so that between 96 and 384 different adaptors, each with a different pair of identical barcodes are added to a human genomic sample. In some embodiments, the number of UIDs in the reaction can be in excess of the number of molecules to be labelled. A person of ordinary skill would recognize that the number of barcodes depends on the complexity of the sample (i.e., expected number of unique target molecules) and would be able to create a suitable number of barcodes for each experiment.

Briefly, one embodiment, the invention is a method for enrichment of multiple one target nucleic acids in a library of a larger number of nucleic acids, specifically, enrichment of a repertoire of rearranged immune sequences (rearranged T-cell receptor (TCR) genes or rearranged immunoglobulin (Ig) genes) in a library of all genomic sequences derived from a sample. The method includes hybridizing a first oligonucleotide to a target rearranged immune sequence in the library. Each of the nucleic acids in the library of may comprise a first adaptor at the first end and a second adaptor at the second end of the nucleic acid. The method further includes extending the hybridized first oligonucleotide with a first polymerase, thereby producing a first primer extension complex comprising a duplex of the target sequence and the extended first oligonucleotide.

The method further includes capturing the first primer extension complex and enriching the first primer extension complex relative to the library of nucleic acids. The extension product of the first oligonucleotide may be captured via the capture moiety present on the first oligonucleotide. Alternatively, the method may utilize a capture oligonucleotide, for example, an oligonucleotide complementary to at least a portion of the first oligonucleotide. In that embodiment, the first oligonucleotide may comprise a universal sequence at least partially complementary to the capture oligonudeotide. The capture oligonudeotide may comprise a capture moiety and may be bound to a solid matrix via the capture moiety.

The method further comprises hybridizing a second oligonudeotide to the target rearranged immune sequence in captured and enriched first primer extension complex, and extending the hybridized second oligonudeotide with a second polymerase, thereby producing a second primer extension complex comprising a duplex of the target nucleic acid and the extended second oligonucleotide, thereby liberating the extended first oligonucleotide from the first primer extension complex. The method can further include amplifying the target nucleic acid from the second primer extension complex with a third polymerase and first and second amplification primers. The amplification primers may have regions of complementarity with primer binding sites in the first and second adaptors at the ends of the target nucleic acid.

In another embodiment, the present disclosure provides for a kit for assessing the repertoire of rearranged immune sequences in a library of nucleic acids. The kit can include a set of first oligonucleotides complementary to rearranged immune sequences and a set of second oligonucleotides complementary to a different sequence within the same rearranged immune sequences. In some embodiments, the second oligonucleotide hybridizes to the target nucleic acid at a position 5' to the first oligonudeotide. The kit may also comprise adaptors to be added to the nucleic acids in the sample to form a library and a first and second amplification primers complementary to primer binding sites in the adaptors. The first oligonucleotides in the set can include a capture moiety. Alternatively, the kit may comprise a capture oligonucleotide complementary to at least a portion of the first oligonucleotides in the set where the first oligonucleotides comprise a universal sequence at least partially complementary to the capture oligonucleotide. The capture oligonucleotide may comprise a capture moiety and may be bound to solid matrix via the capture moiety or have the capture moiety supplied separately in the kit. The second oligonucleotide can hybridize to the target nucleic acid at a position 5' to the first oligonucleotide. The first amplification primer has a 3' end complementary to the first adapter and the second amplification primer has a 3' end complementary to the second adapter.

In yet another embodiment, the present disclosure provides for a composition, including a library of nucleic acids including rearranged immune sequences. Each of the nucleic acids in the library of nucleic acids have a first end comprising a first adapter, a second end comprising a second adapter, and a region of interest comprising a rearranged immune sequence intermediate the first adapter and the second adapter. The composition further includes an extended first oligonucleotide hybridized to the region of interest of the target nucleic acid. The extended first oligonucleotide includes at least one capture moiety. The composition further includes a solid support bound to the at least one capture moiety, a second oligonucleotide hybridized to the target nucleic acid at a position 5' to the first extended oligonucleotide, and a polymerase associated with a 3' end of the second oligonudeotide. The composition may further comprise a capture oligonudeotide, for example, an oligonucleotide complementary to at least a portion of the first oligonucleotide. The first oligonucleotide may comprise a universal sequence at least partially complementary to the capture oligonudeotide. The capture oligonudeotide may comprise a capture moiety. The capture oligonudeotide may be bound to a solid matrix (e.g., beads) via the capture moiety.

The methods of the instant invention can be used as a part of a sequencing protocol, including a high throughput single molecule sequencing protocol to assess a repertoire of rearranged immune sequences in an organism. The method of the invention generates a library of target nucleic acids comprising rearranged immune sequences to be sequenced. The target nucleic acids in the library may incorporate barcodes for molecular identification and sample identification.

The present invention comprises at least one linear primer extension step with a target specific primer. The linear extension step has several advantages over exponential amplification practiced in the art. Each target nucleic acid is characterized by a unique rate of synthesis that depends on the rate of annealing of the target-specific primer and the rate with which a polymerase can read through a particular target sequence. Differences in the rate of extension and the rate of synthesis create a bias that may result in a slight difference in a single round of synthesis. However, the slight difference becomes exponentially amplified during PCR. The resulting gap is referred to as PCR bias. The bias may obscure any difference in the initial quantities of each sequence in the sample and preclude any quantitative analysis. (See US20170037459A1, US20180023131, US20180087108 and WO2019121842.

In some embodiments, the instant method includes a preliminary step of preparing nucleic acid library fragments from a sample. The nucleic acids in a sample are optionally fragmented and adapters are ligated to each end of the nucleic acids. Suitable methods for preparing libraries of nucleic acid fragments for use with the present disclosure include transposon-mediated fragmentation and labeling, mechanical shearing, enzymatic digestion, overhang (e.g., T/A) or blunt end ligation, template-switching mediated adapter ligation, the like and combinations thereof. Ultimately, this step results in a library of nucleic acids, where each of the nucleic acids has a first end comprising a first adapter and a second end comprising a second adapter. Notably the first and second adapter can be the same or different and can further take on various morphologies including, but not limited to, forked or Y-shaped adapters having a complementary portion and a non-complementary portion, blunt end adapters, overhang adapters, hairpin adapters, stem-loop adaptors and the like as long as a ligation reaction can be performed to ligate the adaptor to the single stranded or double-stranded nucleic acid. Moreover, in the case of hairpin adapters, it may be useful to include a blocking element (e.g., a 3' dideoxynucleotide or phosphate group) to prevent self-priming events.

As discussed further below, the instant invention includes a library of rearranged immune sequences generated from the starting library of all genomic nucleic acids.

In some embodiments, the method of the invention includes one or more purification steps after the primer extension. In some embodiments, the primers and large-size template DNA are separated from the extension products by a size-exclusion method, for example, gel electrophoresis, chromatography or isotachophoresis or epitachophoresis.

In some embodiments, purification is by affinity binding. In variations of this embodiment, the affinity is to the specific target sequence (sequence capture). In other embodiments, the primer comprises an affinity tag. Any affinity tag known in the art can be used, such as biotin or an antibody or an antigen for which a specific antibody exists. The affinity partner for the affinity tag may be present in solution, e.g., on a solution-phase solid support, such as suspended particles or beads, or bound to solid-phase support. In the course of affinity purification, unbound components of the reaction mixture are washed away. In some embodiments, additional steps are taken to remove unused primer. In some embodiments, the affinity capture alters the charge of the primer extension product. For example, the inclusion of one or more biotinylated nucleotides and binding or streptavidin thereto creates an altered charge on the nascent nucleic acid strand. The altered charge can be utilized for separation of the nascent strand (the primer extension product) by isotachophoresis or epitachophoresis.

In some embodiments, the amplification of the captured and enriched target nucleic acid is exponential and involves PCR. It is desired to reduce PCR amplification bias. If one or more gene-specific primers are used, to reduce bias, the method involves a limited number of amplification cycles (e.g., about 10 or fewer cycles). If universal primer is used, bias is generally believed to be minimized. In that embodiment, a single universal primer can be used to synthesize both strands. In other embodiments, the extension primer (or adapter) on one side and the adapter on the other side of the molecule to be amplified contain different universal primer binding sites. A universal primer may be paired with another universal primer (of the same or different sequence). In other embodiments, the universal primer may be paired with a gene-specific primer. Because PCR with universal primers has reduced sequence bias, the number of amplification cycles need not be limited to the same extent as in PCR with gene-specific primers. The number of amplification cycles where universal primers are used can be low but also can be as high as about 20, 30 or more cycles.

There are various ways to provide universal primer binding sites to enable amplification with universal primers. In some embodiments, the invention includes adding a homopolymer tail to the 3' end of a nucleic acid. In this embodiment, the homopolymer may serve as a binding site for the reverse complement homopolymer (poly-A/poly-T).

In some embodiments described above, the method involves a target-specific primer that includes a universal priming sequence ("priming site") and yields a primer extension product with a single priming site. In such embodiments, only one additional priming sequence ("priming site") needs to be provided to enable exponential amplification. In other embodiments, the target-specific primer does not include a universal priming site. In such embodiments, two priming sites (e.g., in each of the adaptors) are needed to enable exponential amplification.

One example of a single-strand ligation method can be used in embodiments where the extension primer comprises a universal ligation site. In such embodiments, the adapter having a double-stranded region and a single stranded overhang complementary to the universal ligation site in the primer may be annealed and ligated. Annealing of the single stranded 3'-overhang of the adapter to the universal ligation site at the 5'-end of the primer creates a double stranded region with a nick in the strand containing the primer extension product. The two strands can be ligated at the nick by a DNA ligase or another enzyme, or a non-enzymatic reagent that can catalyze a reaction between the 5'-phosphate of the primer extension product and the 3'-OH of the adapter. The adapter may comprise a universal priming site at one end of the primer extension product.

Another example of a single-strand ligation method can be used to add the universal priming site to the opposite end of the primer extension product (or, in embodiments where the extension primer does not comprise a universal ligation site, to both sides of the extension product). For this embodiment, one or both ends of the primer extension product to be ligated do not have a universal ligation site. Further, in some embodiments, at least one end of the primer extension product to be ligated has an unknown sequence (e.g., due to a random termination event or an unknown sequence variation.). In such embodiment, a sequence-independent single-strand ligation method is employed. An exemplary method is described in a U.S. Application Pub. No. 20140193860. Essentially, the method uses a population of adapters where the single-stranded 3'-end overhang instead of having a universal ligation site, has a random sequence, e.g., a random hexamer sequence. In some embodiments of that method, the adapter also has a hairpin structure. Another example is a method enabled by ACCEL-NGS IS DNA Library Kit (Swift Biosciences, Ann Arbor, Mich.).

The ligation step of the method utilizes a ligase or another enzyme with a similar activity or a non-enzymatic reagent. The ligase can be a DNA or RNA ligase, e.g., of viral or bacterial origin such as T4 or *E. coli* ligase, or thermostable ligases Afu, Taq, Tfl or Tth. In some embodiments, an alternative enzyme, e.g., topoisomerase can be used. Further, a non-enzymatic reagent can be used to form the phosphor-diester bond between the 5'-phosphate of the primer extension product and the 3'-OH of the adapter as described and referenced in U.S. Pat. App. Pub. 2014/0193860.

In some embodiments of the method, the first ligation of the adapter is followed by an optional primer extension. The ligated adapter has a free 3'-end that can be extended to create a double-stranded nucleic acid. The end opposite the adapter will then become suitable for a blunt-end ligation of another adapter. Avoiding the need for a single-strand ligation procedure, this double stranded end of the molecule can be ligated to a double stranded adapter by any ligase or another enzymatic or non-enzymatic means. The double stranded adapter sequence supplies one or more universal priming sites (for amplification or sequencing) and optionally, one or more barcodes.

In some embodiments, the enriched rearranged immune sequences are sequenced. Any of a number of sequencing technologies or sequencing assays can be utilized. The term “Next Generation Sequencing (NGS)” as used herein refers to sequencing methods that allow for massively parallel sequencing of clonally amplified molecules and of single nucleic acid molecules.

Non-limiting examples of sequence assays that are suitable for use with the methods disclosed herein include nanopore sequencing (US Pat. Publ. Nos. 2013/0244340, 2013/0264207, 2014/0134616, 2015/0119259 and 2015/0337366), Sanger sequencing, capillary array sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), sequencing by hybridization (Drmanac et al., *Nature Biotech.,* 16:54-58 (1998), and NGS methods, including but not limited to sequencing by synthesis (e.g., HiSeq“, MiSeq”, or Genome Analyzer, each available from Illumina), sequencing by ligation (e.g., SOLiD™, Life Technologies), ion semiconductor sequencing (e.g., Ion Torrent™, Life Technologies), and SMRT® sequencing (e.g., Pacific Biosciences).

Commercially available sequencing technologies include: sequencing-by-hybridization platforms from Affymetrix Inc. (Sunnyvale, Calif.), sequencing-by-synthesis platforms from Illumina/Solexa (San Diego, Calif.) and Helicos Biosciences (Cambridge, Mass.), sequencing-by-ligation platform from Applied Biosystems (Foster City, Calif.). Other sequencing technologies include, but are not limited to, the Ion Torrent technology (ThermoFisher Scientific), and nanopore sequencing (Genia Technology from Roche Sequencing Solutions, Santa Clara, Calif.); and Oxford Nanopore Technologies (Oxford, UK).

In some embodiments, the sequencing step involves sequence aligning. In some embodiments, aligning is used to determine a consensus sequence from a plurality of sequences, e.g., a plurality having the same unique molecular ID (UID). In some embodiments, aligning is used to identify sequence variations, such as single nucleotide variations (SNV). In some embodiments, a consensus sequence is determined from a plurality of sequences all having an identical UID. In other embodiments, UID is used to eliminate artifacts, i.e., variations existing in the progeny of a single molecule (characterized by a particular UID). Such artifacts resulting from PCR errors or sequencing errors can be eliminated using UIDs.

In some embodiments, the number of each sequence in the sample can be quantified by quantifying relative numbers of sequences with each UID among the population having the same multiplex sample ID (MID). Each UID represents a single molecule in the original sample and counting different UIDs associated with each sequence variant can determine the fraction of each sequence variant in the original sample, where all molecules share the same MID. A person skilled in the art will be able to determine the number of sequence reads necessary to determine a consensus sequence. In some embodiments, the relevant number is reads per UID (“sequence depth”) necessary for an accurate quantitative result. In some embodiments, the desired depth is 5-50 reads per UID.

In some embodiments, the method involves a use of a genomic library or an expression library that comprises a plurality of polynucleotides. In some embodiments, a library of rearranged immune sequences is formed according to the method of the invention. A library can be stored and used multiple times for further amplification or sequencing of the nucleic acids in the library.

The instant invention is described in more detail in reference to FIGS. 1-6. Referring to FIG. 1, in one embodiment, the instant method includes a first primer extension step. A target nucleic acid comprising a rearranged immune sequence comprising V, D and J regions is shown as an example. The target nucleic acid is present in the adapted form, i.e., has an adaptor on each end. The first oligonucleotide primer (capture primer) comprising a V-gene specific sequence is shown as an example. The capture primer comprises a capture moiety (biotin or another moiety or a universal capture sequence as described herein). The capture primer is hybridized to the rearranged immune sequence in the library of nucleic acids and extended by a polymerase to form a first extension product (dotted line) complexed with the target nucleic acids in the extension duplex.

In some embodiments, the capture primer comprises a capture sequence that is at least partially complementary to a capture oligonucleotide. This sequence may be referred to as “universal capture sequence.” The capture oligonucleotide contains a sequence at least partially complementary to the capture sequence in the first primer. The capture oligonucleotide may be referred to as “universal capture oligonucleotide.” The capture oligonucleotide is non-extendable by a nucleic acid polymerase and cannot itself serve as a primer. In some embodiments, the capture oligonucleotide comprises a capture moiety. In other embodiments, the capture oligonucleotide is attached to solid support.

The length of the extension product can be controlled actively through techniques such as inactivating the polymerase or by limiting essential reagents. In some embodiments, the reaction is stopped by elevating the temperature to inactivate a non-thermostable polymerase. In yet other embodiments, the reaction is stopped by the addition of a chelator, such as EDTA.

Another method of controlling the length of primer extension products is the addition of terminator nucleotides, including reversible terminator nucleotides. One skilled in the art is able to experimentally or theoretically determine a proper ratio of terminator and non-terminator nucleotides that allows for limited primer extension to yield predominantly the desired length product. Examples of terminator nucleotides include dideoxynucleotides, 2'-phosphate nucleotides as described in U.S. Pat. No. 8,163,487 to Gelfand et al., 3'-O-blocked reversible terminators, and 3'unblocked reversible terminators as described e.g., in U. S. Pat. App. Pub. No. 2014/0242579 to Zhuo et al., and Guo, J., et al., *Four-color DNA sequencing with 3'-O-modified nucleotide reversible terminators and chemically cleavable fluorescent dideoxynucleotides*, P.N.A.S. 2008 105 (27) 9145-9150.

The extension duplex is captured on solid support using the capture moiety while the non-captured nucleic acids (including non-target nucleic acids) are separated from the extension duplexes containing target nucleic acids. The solid support can be a solution-phase support (e. g., a bead or another like particle), or a solid-phase support (e.g., a silicon wafer, a glass slide, or the like). The solid support 318 can be a solution-phase support (e. g., a bead or another like particle), or a solid-phase support (e.g., a silicon wafer, a glass slide, or the like).

In various embodiments of the present disclosure, the capture oligonucleotide primer can include one or more modified bases, capture moieties or a combination thereof. In the case that the first oligonucleotide primer includes a capture moiety, the first oligonucleotide primer can be attached to a solid support or be free in solution (i.e., not bound or otherwise attached to a solid support) prior to hybridizing the capture oligonucleotide primer to the target nucleic acid. In embodiments where the capture primer is not attached to a solid support via the capture moiety, the hybridization and extension steps take place in solution.

Figure 2:
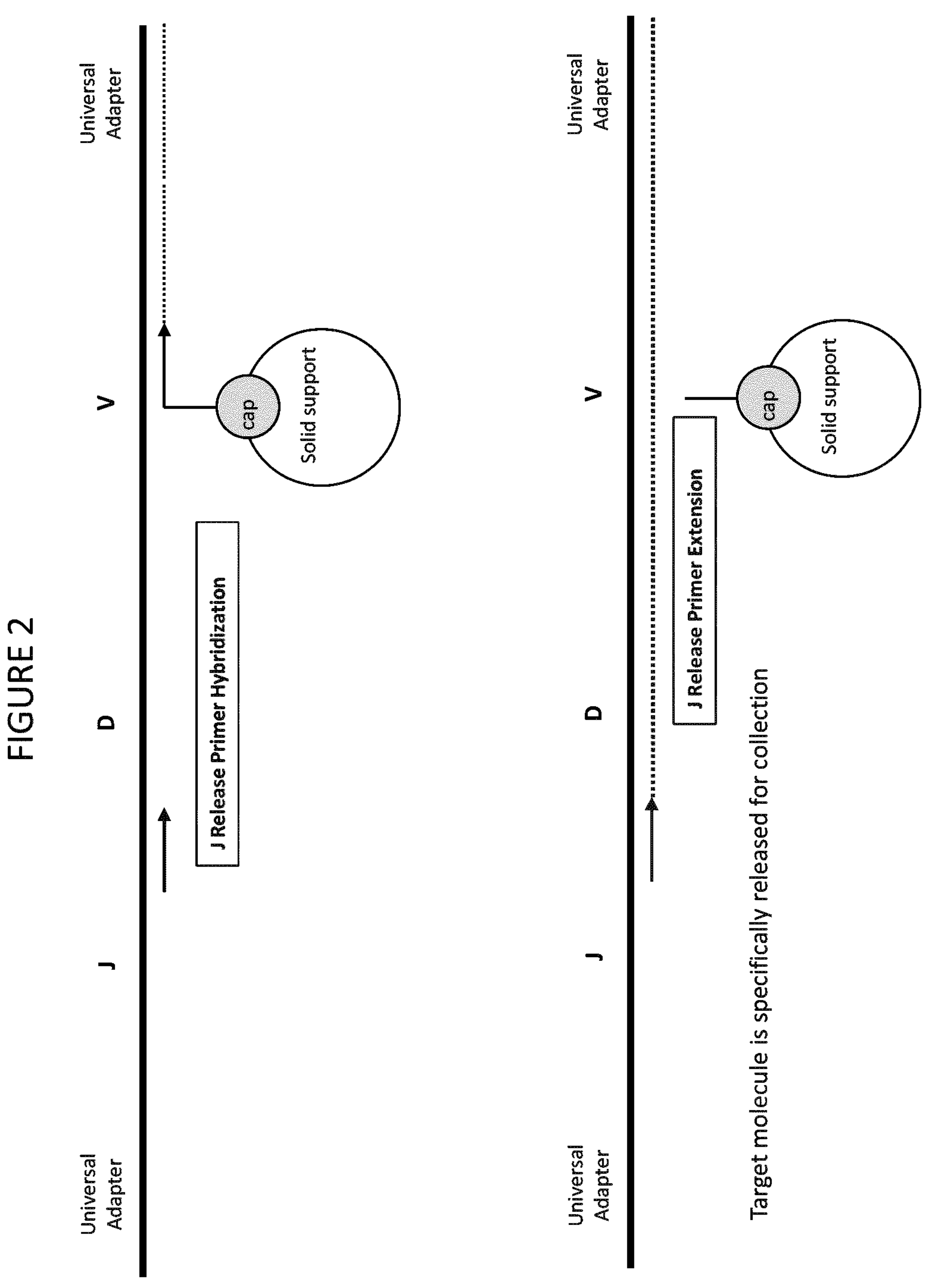
FIG. 2 is a diagram of the steps in first embodiment of the workflow.

Referring now to FIG. 2, the next step includes a second primer extension step. The target nucleic acid comprising a rearranged immune sequence comprising V, D and J regions is shown as an example. The second oligonucleotide primer (release primer) comprising a J-gene specific sequence is shown as an example. In general, the release primer hybridizes 5'-relative to the capture primer. The release primer is hybridized to the rearranged immune sequence in the first extension duplex captured after the capture primer extension. The release primer is extended by a polymerase to form a second extension product (dotted line) complexed with the target nucleic acids in a second extension duplex. The length of the extension product can be controlled actively through techniques such as inactivating the polymerase or by limiting essential reagents. The first primer extension product is freed from the duplex. In some embodiments, the first primer extension product is released into solution by a strand displacement activity of the polymerase. In other embodiments, primer extension product is hydrolyzed by the 5'-3' activity of the polymerase. The 5'-3' activity of the polymerase may comprise a combination of 5'-3' exonuclease activity and flap endonuclease activity. By dissociating from the first primer extension product, the second extension duplex comprising the target nucleic acid is released from solid support and is available for collection and further analysis.

Figure 3:
FIG. 3 is a diagram of the final steps in first embodiment of the workflow.

Referring to FIG. 3, in some embodiments, the method further includes an optional step of amplification. As shown in FIG. 3, each of the adaptors on the ends of the captured target sequence released from the comprises an adaptor on each end wherein the adaptor comprises a primer binding site. In some embodiments, the adaptor comprises a binding site for a universal primer capable of directing universal amplification. This step can involve linear or exponential amplification (e.g., PCR). The amplification step includes amplifying the target nucleic acid with a third polymerase, a first amplification primer, and a second amplification primer. In some embodiments, adaptors comprise sequences (e.g., a 3'-portion) complementary to primer binding sites in adaptors. In other embodiments, the primers for amplification can include any sequences that are present within the target nucleic acid being amplified (e.g., V, D, or J sequences).

Figure 4:
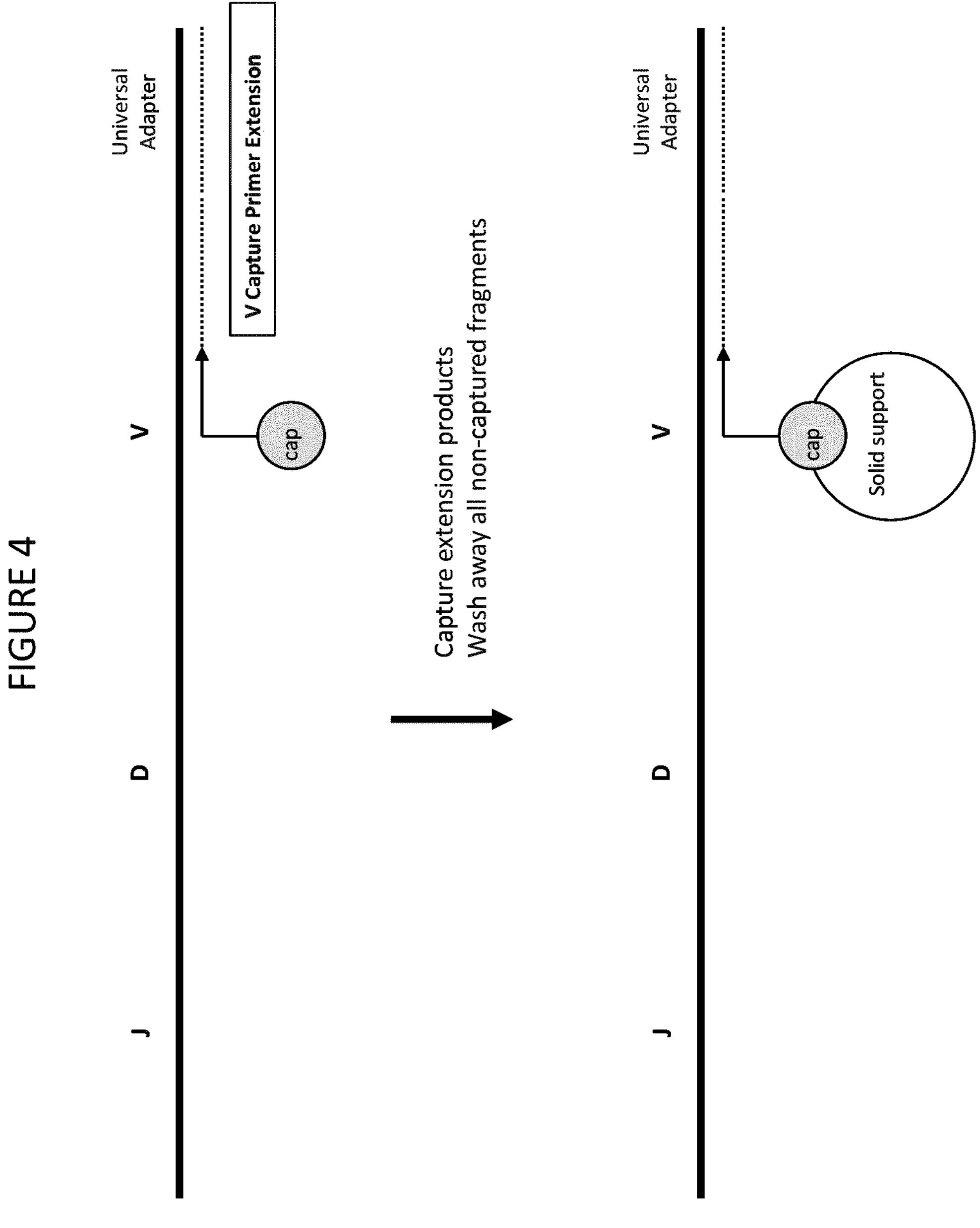
FIG. 4 is a diagram of the initial steps in another embodiment of the workflow.

Referring to FIG. 4, in another embodiment, the instant method includes a first primer extension step. A target nucleic acid comprising a rearranged immune sequence comprising V, D and J regions is shown as an example. Unlike in the embodiment shown on FIG. 1, the target nucleic acid is attached to an adaptor on only one end. The first oligonucleotide primer (capture primer) comprising a V-gene specific sequence is shown as an example. The capture primer comprises a capture moiety (biotin or another moiety or a universal capture sequence as described herein). The capture primer is hybridized to the rearranged immune sequence in the library of nucleic acids and extended by a polymerase to form a first extension product (dotted line) complexed with the target nucleic acids in the extension duplex.

In some embodiments, the capture primer comprises a capture sequence that is at least partially complementary to a capture oligonucleotide. This sequence may be referred to as "universal capture sequence." The capture oligonucleotide contains a sequence at least partially complementary to the capture sequence in the first primer. The capture oligonucleotide may be referred to as "universal capture oligonucleotide." The capture oligonucleotide is non-extendable by a nucleic acid polymerase and cannot itself serve as a primer. In some embodiments, the capture oligonucleotide comprises a capture moiety. In other embodiments, the capture oligonucleotide is attached to solid support.

As described in connection with the embodiment shown in FIG. 1, the length of the extension product can be controlled actively through techniques such as inactivating the polymerase (using heat or a chelator) or by limiting essential reagents, or by the addition of terminator nucleotide. As also described in connection with the embodiment shown in FIG. 1, the extension duplex is captured on solid support using the capture moiety and separated from any non-captured nucleic acids.

Figure 5:
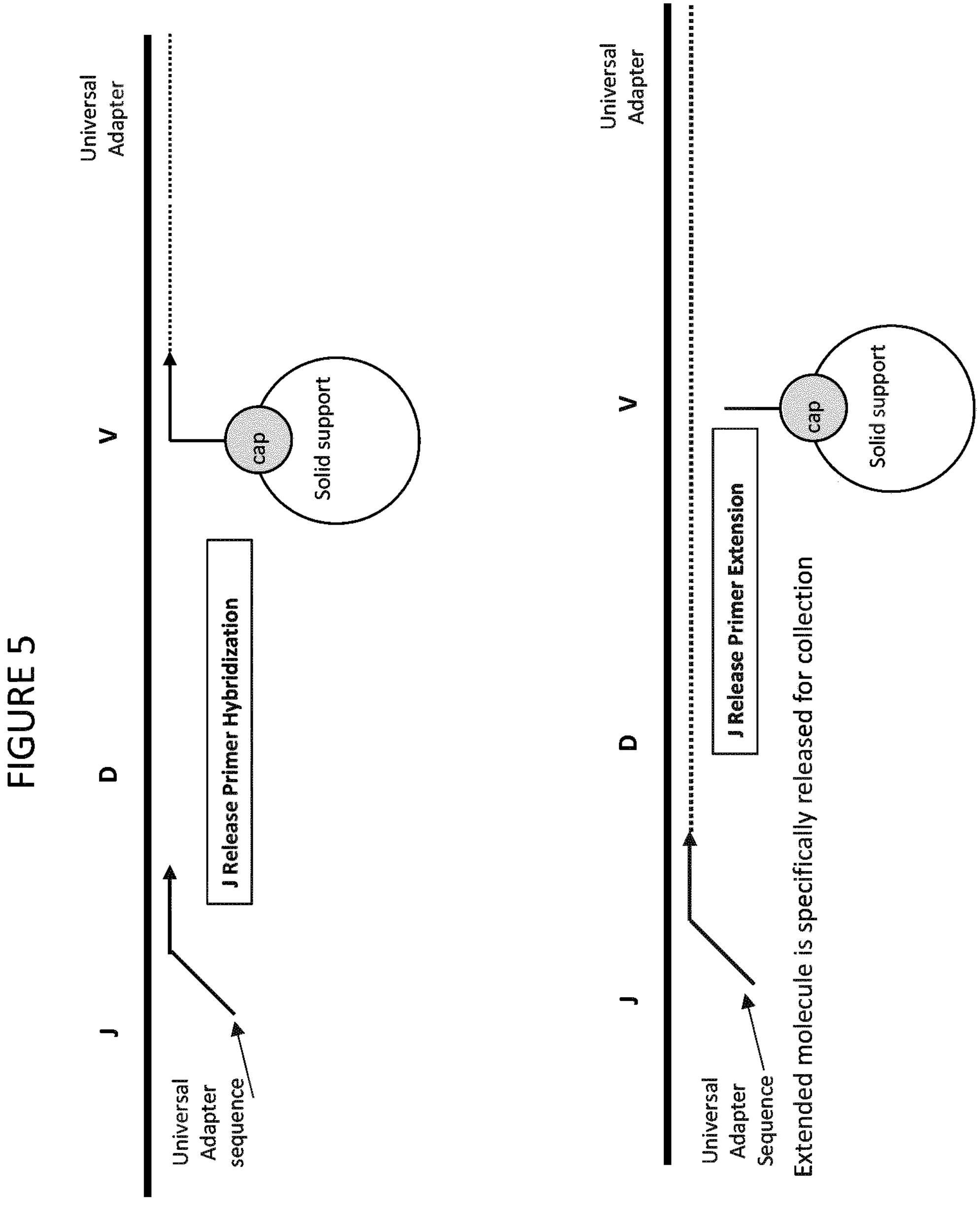
FIG. 5 is a diagram of the steps in another embodiment of the workflow.

Referring now to FIG. 5, the next step includes a second primer extension step. The target nucleic acid comprising a rearranged immune sequence comprising V, D and J regions is shown as an example. The second oligonucleotide primer (release primer) comprising a J-gene specific sequence is shown as an example. Unlike in the embodiment shown in FIG. 2, the release primer comprises universal adaptor sequences. The universal sequences may be placed at or near the 5'-end of the primer and distal to the target binding potion of the release primer. In general, the release primer hybridizes 5'-relative to the capture primer on the target nucleic acid. The release primer is hybridized to the rearranged immune sequence in the first extension duplex captured after the capture primer extension. The release primer is extended by a polymerase to form a second extension product (dotted line) complexed with the target nucleic acids in a second extension duplex. The length of the extension product can be controlled actively through techniques such as inactivating the polymerase or by limiting essential reagents. The first primer extension product is freed from the duplex. In some embodiments, the first primer extension product is released into solution by a strand displacement activity of the polymerase. In other embodiments, primer extension product is hydrolyzed by the 5'-3' activity of the polymerase. The 5'-3' activity of the polymerase may comprise a combination of 5'-3' exonuclease activity and flap endonuclease activity. By dissociating from the first primer extension product, the second extension duplex comprising the target nucleic acid is released from solid support and is available for collection and further analysis.

Figure 6:
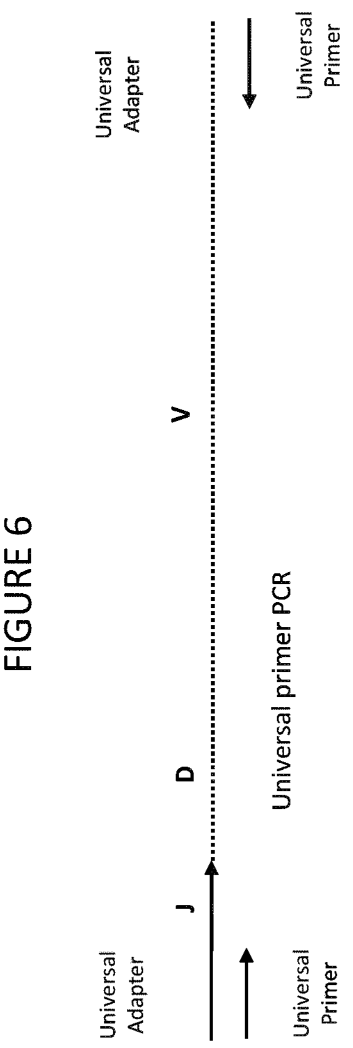
FIG. 6 is a diagram of the final steps in another embodiment of the workflow.

Referring to FIG. 6, in some embodiments, the method further includes an optional step of amplification. As shown in FIG. 6, a universal sequence (or a complement thereof) is present on both ends of the second primer extension product. On one end the universal sequence is part of the adaptor while on the other end, the universal sequence was part of the release primer. In some embodiments, the universal sequence introduced by the adaptor or the primer comprises a binding site for a universal primer capable of directing universal amplification. The amplification step can involve linear or exponential amplification (e.g., PCR). The amplification step includes amplifying the target nucleic acid with a third polymerase, a first amplification primer, and a second amplification primer. In some embodiments, the third and fourth primers are universal primers binding to the universal binding sites. In other embodiments, the primers for amplification can include any sequences that are present within the target nucleic acid being amplified (e.g., V, D, or J sequences).

In some embodiments (e.g., those shown in FIG. 1-3 or 4-6), the method enables selective amplification of the target nucleic acids comprising rearranged immune sequences from the library of nucleic acids while avoiding amplification of either of the first or second extension products. In one example, dUTPN and a uracil-compatible DNA polymerase (e.g., KAPA HiFi uracil+DNA polymerase (KAPA Biosystems, Wilmington, Mass., or Phusion U DNA polymerase (ThermoFishger Scientific, Waltham, Mass.) are included in one or both of the first and second extension reactions. The resulting extension products will include at least one uracil nucleotide, whereas the target nucleic acid template can be a DNA template having no uracil nucleotides. Thereafter, a uracil incompatible polymerase (e.g., KAPA HiFi DNA polymerase (KAPA Biosystems, Wilmington, Mass., or Phusion High Fidelity DNA polymerase (ThermoFishger Scientific, Waltham, Mass.) is used in the amplification step and amplification of the uracil-containing extension products is avoided. Alternatively, or in addition, uracil-containing products can be selectively digested or otherwise degraded, e.g., by the addition of Uracil-N-DNA glycosylase (UNG), optionally in the presence of primary amines as described in U.S. Pat. No. 8,669,061, leaving behind only the original target molecules from the library of nucleic acids.

In some embodiments, the method further comprises assessment of a status of a subject (e.g., a patient). In some embodiments, in addition to enriching for and determining the sequence of the patient's immune repertoire (a repertoire of somatically rearranged immune sequences), the method further comprises determining in the patient's sample, the sequence of disease biomarkers including somatically rearranged biomarkers of disease. The method further comprises diagnosis of disease in the patient or selecting or changing a treatment based on the sequence of disease biomarkers and the status of the patient's immune profile. In some embodiments, the disease biomarkers are selected from Table 3(a), (b) and (c).

In some embodiments, in addition to enriching for and determining the sequence of the patient's immune repertoire (a repertoire of somatically rearranged immune sequences), the method further comprises determining in the patient's sample, the sequence and optionally amount of RNA transcripts of immune cell markers further characterizing the status of the patient. The additional sequences are selected from markers of T-cell type, T-cell exhaustion, T-cell activation, markers of tissue-resident memory cell, markers and markers of tumor-reactive T-cells. The additional targets sequences may be transcripts of one or more of CD45, CD3, CD8, CD39, CD25, IL-7R, CD4, CXCR3, CCR6, CD3G, CD3D, CD3E, CD2, CD8A, GZMA FOXP3, CD19, CD79A, PDCD1, HAVCR2, IFNG, TNF, ITGAE, CXCR6, (see Yost et al. (2019) *Clonal replacement of tumor specific T-cells following PD-*1 *blockade*, Nature Medicine, doi.org/10.1038/s41591-019-0522-3. The method further comprises diagnosis of disease in the patient or selecting or changing a treatment based on the sequence of T-cell markers and the status of the patient's immune profile.

EXAMPLES

Example 1: Determining Immune Profile from a Human T Cell DNA Library

In this example, the method of the invention was applied to a human T-lymphocyte library. A human PanT cell library (comprising DNA isolated from blood-derived CD3+ cells) was obtained from StemCell Technologies (Cambridge, Mass.). 50 ng of library DNA was used. V capture primers were designed with a 5' biotin and J release primers were designed without biotins (Tables 1 and 2). These primers were added to primers targeting biomarkers in Table 3(a) containing approximately 1,500 other capture and release primer sets. The library was purified and amplified using the KAPA HyperPlus shotgun library using 8 cycles of PCR. The capture and extension reaction was set up as follows:

| | (uL) |
|---|---|
| genomic library | 30 |
| 2G polymerase Master Mix (5x) | 11 |
| Water | 0 |
| Capture Primers (10 uM total primer concentration) | 1.5 |
| dATP (100 mM) | 1.9 |
| MgCl2 (50 mM) | 5 |
| Universal blocking oligo (74.6 uM) | 5.54 |
| Total | 54.94<br>25 per tube |

The annealing and extension steps were carried out in a thermocycler using the following temperature profile:

| | |
|---|---|
| Denaturation | 95° C. |
| Quick temp drop | 80° C. |
| slow temp drop (~0.1° C. per second or 0.1% speed) | |
| Annealing | 60° C. |
| Extension | 65° C. |

The first extension complex was captured on Dynabeads MyOne Streptavidin T1 beads (ThermoFisher Scientific, Waltham, Mass.) according to manufacturer's recommendations. Three successive washes were performed in the following wash buffer:

| Component | Final 2X Concentration |
|---|---|
| 1M Tris-HCl (pH 8) | 40 mM |
| 500 mM EDTA | 2 mM |
| 5M NaCl | 2M |
| Tween (10%) | 0.20% |
| Water | Fill to 50 mL |

The captured purified first extension complex was resuspended in 20 uL 10 mM Tris pH 8, 0.1% Tween buffer.

The second round of hybridization (to the release primer) was performed under the following conditions:

| | [uL] |
|---|---|
| Captured first extension complex | 20 |
| Release Primers (100 uM total primer concentration) | 2 |

-continued

| | [uL] |
|---|---|
| Water | 18 |
| Kapa 2G Buffer A (5x) | 10 |
| TOTAL | 50<br>30 per tube |

Annealing was allowed to proceed for 30 minutes at 55° C. The complex with the release was captured from the reaction mixture with a magnet, washed twice in 120 uL of 10 mM Tris, 0.1% Tween 20 buffer and resuspended in 20 uL 10 mM Tris pH 8, 0.1% Tween buffer.

The second extension reaction was set up as follows:

| | [uL] |
|---|---|
| Template* | 20 |
| Water | 18 |
| Kapa 2G Buffer A (5x) | 10 |
| dNTPs (10 mM) | 1 |
| Kapa 2G Fast (5 U/uL) | 1 |
| TOTAL | 50<br>30 per tube |

*First extension complex with annealed release primer

Extension was allowed to proceed at 50° C. Released extension products were captured with SPRI beads and washed according to manufacturer's recommendations and eluted with the PCR mix shown below.

Amplification by PCR with universal primers was performed as follows:

| PCR mix | |
|---|---|
| HiFi HS RM 2X | 25 |
| Kapa Library Amp Primers | 5 |
| Water | 20 |
| Total | 50 |

| Temp (° C.) | Time | Cycles |
|---|---|---|
| 98 | 45 sec | |
| 98 | 15 s | 15 |
| 60 | 30 s | |
| 72 | 30 s | |
| 72 | 1 min | |

Amplification products were captured and washed with SPRI beads according to manufactures' recommendations and eluted in 20 uL 10 mM Tris pH 8, 0.1% Tween buffer.

Figure 7:
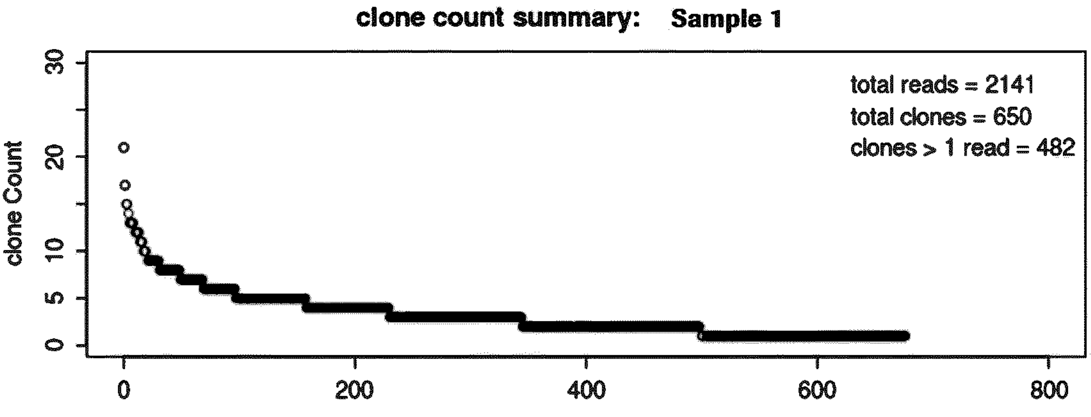
FIG. 7 shows experimental results obtained with the method of the invention.
Figure 7:
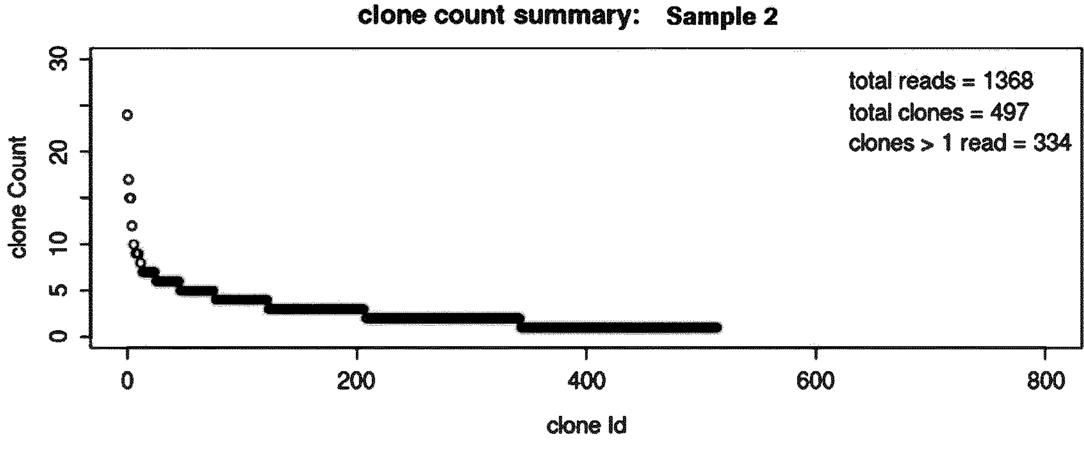
Figure 7:
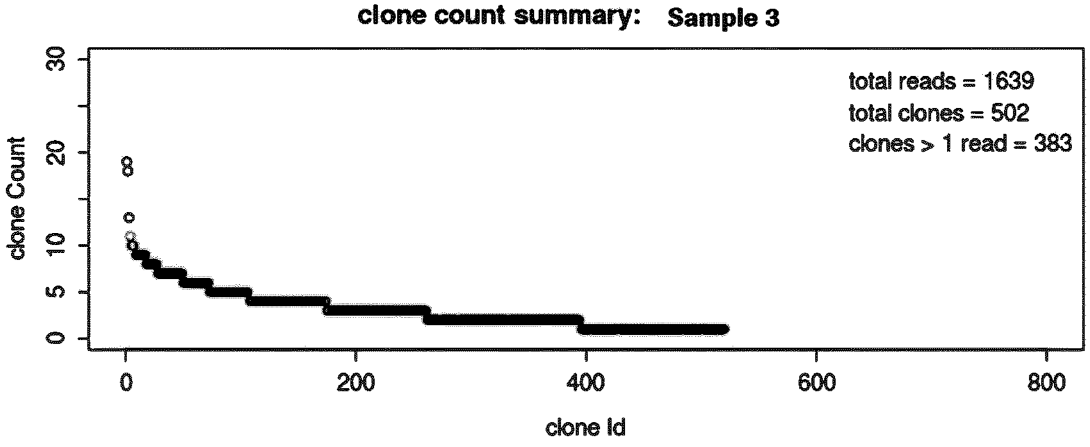

Results are shown in the table below and in FIG. 7.

| Sample | Reads | Clones* | V genes | J genes |
|---|---|---|---|---|
| 1 | 2141 | 650 | 50 | 20 |
| 2 | 1368 | 497 | 48 | 15 |
| 3 | 1639 | 502 | 50 | 14 |

*number of clones is the number of unique CDR3 regions identified

While the invention has been described in detail with reference to specific examples, it will be apparent to one skilled in the art that various modifications can be made within the scope of this invention. Thus the scope of the invention should not be limited by the examples described herein, but by the claims presented below.

The invention claimed is:

1. A method for enrichment of at least one target nucleic acid in a library of nucleic acids, wherein the at least one target nucleic acid includes a rearranged immune sequence having a V gene, a D gene, and a J gene, wherein the method comprises the following steps:

(a) providing the at least one target nucleic acid, wherein the at least one target nucleic acid includes at least one adaptor;

(b) hybridizing a first oligonucleotide to the at least one target nucleic acid, wherein the first oligonucleotide comprises (i) a sequence complementary to the V gene of the rearranged immune sequence of the at least one nucleic acid, and (ii) a capture moiety;

(c) extending the hybridized first oligonucleotide with a first polymerase, thereby producing a first primer extension complex, wherein the first primer extension complex comprises the at least one target nucleic acid and the extended first oligonucleotide;

(d) capturing the first primer extension complex via the capture moiety of the first oligonucleotide;

(e) hybridizing a second oligonucleotide comprising a sequence complementary to the J gene to the rearranged immune sequence in the captured first primer extension complex; and (f) extending the hybridized second oligonucleotide with a second polymerase, thereby producing a second primer extension complex, wherein the second primer extension complex comprises the at least one target nucleic acid and the extended second oligonucleotide, thereby liberating the extended first oligonucleotide, wherein the at least one target nucleic acid within the second primer extension complex is enriched relative to the library of nucleic acids.

2. The method of claim 1, further comprising amplifying the at least one target nucleic acid.

3. The method of claim 1, wherein the second polymerase has a strand displacement activity.

4. The method of claim 1, further comprising the following step: (g) sequencing the target nucleic acid.

5. The method of claim 1, wherein the capture moiety of the first oligonucleotide is selected from a capture sequence, a chemical moiety for which a ligand is available or an antigen for which an antibody is available.

6. The method of claim 5, wherein the capture moiety is a capture sequence complementary to a capture oligonucleotide, which comprises a modified nucleotide increasing the melting temperature of the capture oligonucleotide.

7. The method of claim 1, wherein the first oligonucleotide is bound to a solid support via the capture moiety prior to hybridizing the first oligonucleotide to the target nucleic acid.

8. The method of claim 1, wherein the adaptor comprises at least one barcode.

9. The method of claim 1, wherein the sequence of the first oligonucleotide complementary to a V-gene is any one of SEQ ID NOS: 1-63.

10. The method of claim 1, wherein the sequence of the second oligonucleotide complementary to a J is any one of SEQ ID NOS: 64-76.

11. A method of assessing the status of a patient's immune system by determining the rearranged immune sequences according to the method of claim 1, and further determining the expression of T-cell markers selected from: markers of T-cell type, markers of T-cell exhaustion, markers of T-cell activation, markers of tissue-resident memory cells, and markers of tumor-reactive T-cells.

12. A method for enriching at least one target nucleic acid in a library of nucleic acids, wherein the at least one target nucleic acid includes a gene fusion sequence comprising a first fusion partner sequence and a second fusion partner sequence, wherein the method comprises the following steps: (a) providing the at least one target nucleic acid, wherein the at least one target nucleic acid includes at least one adaptor; (b) hybridizing a first oligonucleotide to the at least one target nucleic acid, wherein the first oligonucleotide comprises a sequence complementary to the first fusion partner and further comprises a capture moiety; (c) extending the hybridized first oligonucleotide with a first polymerase, thereby producing a first primer extension complex comprising the at least one target nucleic acid and the extended first oligonucleotide; (d) capturing the first primer extension complex via the capture moiety of the first oligonucleotide; (e) hybridizing a second oligonucleotide comprising a sequence complementary to the second fusion partner sequence to the same strand of the at least one target nucleic acid to which the first oligonucleotide hybridized in the captured first primer extension complex; (f) extending the hybridized second oligonucleotide with a second polymerase having strand displacement activity along the same strand of the at least one target nucleic acid to which the first oligonucleotide hybridized, thereby producing a second primer extension complex comprising the at least one target nucleic acid and the extended second oligonucleotide, thereby liberating the extended first oligonucleotide; and (g) amplifying the at least one target nucleic acid, thereby enriching the at least one target nucleic acid.

13. A method for enriching at least one target nucleic acid in a library of nucleic acids, wherein the at least one target nucleic acid includes a spliced transcript having a splice site, wherein the method comprises the following steps: (a) providing the at least one target nucleic acid, wherein the at least one target nucleic acid includes at least one adaptor; (b) hybridizing a first oligonucleotide to the at least one target nucleic acid, wherein the first oligonucleotide comprises a sequence complementary to a sequence 3'-of the splice site and further comprises a capture moiety; (c) extending the hybridized first oligonucleotide with a first polymerase, thereby producing a first primer extension complex comprising the at least one target nucleic acid and the extended first oligonucleotide; (d) capturing the first primer extension complex via the capture moiety of the first oligonucleotide; (e) hybridizing a second oligonucleotide comprising a sequence complementary to a sequence 5'-of the splice site to the same strand of the at least one target nucleic acid to which the first oligonucleotide hybridized in the captured first primer extension complex; (f) extending the hybridized second oligonucleotide with a second polymerase having strand displacement activity along the same strand of the at least one target nucleic acid to which the first oligonucleotide hybridized, thereby producing a second primer extension complex comprising the at least one target nucleic acid and the extended second oligonucleotide, thereby liberating the extended first oligonucleotide; and (g) amplifying the at least one target nucleic acid thereby enriching the at least one target nucleic acid.

* * * * *

SEQUENCE LISTING

```
<160> NUMBER OF SEQ ID NOS: 76

<210> SEQ ID NO 1
<211> LENGTH: 26
<212> TYPE: DNA
<213> ORGANISM: Artificial Sequence
<220> FEATURE:
<223> OTHER INFORMATION: single-stranded

<400> SEQUENCE: 1

tataagcgag agctgtcagg gcattc                                          26


<210> SEQ ID NO 2
<211> LENGTH: 41
<212> TYPE: DNA
<213> ORGANISM: Artificial Sequence
<220> FEATURE:
<223> OTHER INFORMATION: single-stranded

<400> SEQUENCE: 2

caactgagaa ttgatcatcg aatatttcag acttctctga g                         41


<210> SEQ ID NO 3
<211> LENGTH: 34
<212> TYPE: DNA
<213> ORGANISM: Artificial Sequence
<220> FEATURE:
<223> OTHER INFORMATION: single-stranded

<400> SEQUENCE: 3
```

ctttgtctgg agatttaggt gagaatcgat ttgg 34

<210> SEQ ID NO 4
<211> LENGTH: 34
<212> TYPE: DNA
<213> ORGANISM: Artificial Sequence
<220> FEATURE:
<223> OTHER INFORMATION: single-stranded

<400> SEQUENCE: 4
ctttgtctgg agatttaggt gagaagcgat ttgg 34

<210> SEQ ID NO 5
<211> LENGTH: 26
<212> TYPE: DNA
<213> ORGANISM: Artificial Sequence
<220> FEATURE:
<223> OTHER INFORMATION: single-stranded

<400> SEQUENCE: 5
atgagctttg tctggagagt caggtg 26

<210> SEQ ID NO 6
<211> LENGTH: 26
<212> TYPE: DNA
<213> ORGANISM: Artificial Sequence
<220> FEATURE:
<223> OTHER INFORMATION: single-stranded

<400> SEQUENCE: 6
atgaactttg tctggagagt caggtg 26

<210> SEQ ID NO 7
<211> LENGTH: 22
<212> TYPE: DNA
<213> ORGANISM: Artificial Sequence
<220> FEATURE:
<223> OTHER INFORMATION: single-stranded

<400> SEQUENCE: 7
gagagctgtt ggggcattca gg 22

<210> SEQ ID NO 8
<211> LENGTH: 24
<212> TYPE: DNA
<213> ORGANISM: Artificial Sequence
<220> FEATURE:
<223> OTHER INFORMATION: single-stranded

<400> SEQUENCE: 8
tagagaactg gcgccctgag aatc 24

<210> SEQ ID NO 9
<211> LENGTH: 31
<212> TYPE: DNA
<213> ORGANISM: Artificial Sequence
<220> FEATURE:
<223> OTHER INFORMATION: single-stranded

<400> SEQUENCE: 9
tatggacgtg gtgagctgag aatcaattag g 31

<210> SEQ ID NO 10
<211> LENGTH: 19
<212> TYPE: DNA

```
<213> ORGANISM: Artificial Sequence
<220> FEATURE:
<223> OTHER INFORMATION: single-stranded

<400> SEQUENCE: 10

catggaactg gcgccctga                                                    19


<210> SEQ ID NO 11
<211> LENGTH: 29
<212> TYPE: DNA
<213> ORGANISM: Artificial Sequence
<220> FEATURE:
<223> OTHER INFORMATION: single-stranded

<400> SEQUENCE: 11

tagggaactg gagacctgag aatctagga                                         29


<210> SEQ ID NO 12
<211> LENGTH: 28
<212> TYPE: DNA
<213> ORGANISM: Artificial Sequence
<220> FEATURE:
<223> OTHER INFORMATION: single-stranded

<400> SEQUENCE: 12

gctgagaatc gatcagggaa gtttcctc                                          28


<210> SEQ ID NO 13
<211> LENGTH: 27
<212> TYPE: DNA
<213> ORGANISM: Artificial Sequence
<220> FEATURE:
<223> OTHER INFORMATION: single-stranded

<400> SEQUENCE: 13

tgacctgaga atcgatcagg gaagttg                                           27


<210> SEQ ID NO 14
<211> LENGTH: 30
<212> TYPE: DNA
<213> ORGANISM: Artificial Sequence
<220> FEATURE:
<223> OTHER INFORMATION: single-stranded

<400> SEQUENCE: 14

tgacctgaga attgatcagg gaagtttcct                                        30


<210> SEQ ID NO 15
<211> LENGTH: 29
<212> TYPE: DNA
<213> ORGANISM: Artificial Sequence
<220> FEATURE:
<223> OTHER INFORMATION: single-stranded

<400> SEQUENCE: 15

cgacctgaaa atctaggagg gaagtttcc                                         29


<210> SEQ ID NO 16
<211> LENGTH: 27
<212> TYPE: DNA
<213> ORGANISM: Artificial Sequence
<220> FEATURE:
<223> OTHER INFORMATION: single-stranded

<400> SEQUENCE: 16

aatctggaga cattgtagcc attgggg                                           27
```

<210> SEQ ID NO 17
<211> LENGTH: 23
<212> TYPE: DNA
<213> ORGANISM: Artificial Sequence
<220> FEATURE:
<223> OTHER INFORMATION: single-stranded

<400> SEQUENCE: 17
ttgtagccat cagggacctc tcc 23

<210> SEQ ID NO 18
<211> LENGTH: 28
<212> TYPE: DNA
<213> ORGANISM: Artificial Sequence
<220> FEATURE:
<223> OTHER INFORMATION: single-stranded

<400> SEQUENCE: 18
gctctggaga cactataacc atcaggga 28

<210> SEQ ID NO 19
<211> LENGTH: 27
<212> TYPE: DNA
<213> ORGANISM: Artificial Sequence
<220> FEATURE:
<223> OTHER INFORMATION: single-stranded

<400> SEQUENCE: 19
gacattgtag ccattgggga cttctcc 27

<210> SEQ ID NO 20
<211> LENGTH: 26
<212> TYPE: DNA
<213> ORGANISM: Artificial Sequence
<220> FEATURE:
<223> OTHER INFORMATION: single-stranded

<400> SEQUENCE: 20
ttgtagccat tcgggacttc tccttt 26

<210> SEQ ID NO 21
<211> LENGTH: 29
<212> TYPE: DNA
<213> ORGANISM: Artificial Sequence
<220> FEATURE:
<223> OTHER INFORMATION: single-stranded

<400> SEQUENCE: 21
gatctggaga cattgtagcc attgggaac 29

<210> SEQ ID NO 22
<211> LENGTH: 32
<212> TYPE: DNA
<213> ORGANISM: Artificial Sequence
<220> FEATURE:
<223> OTHER INFORMATION: single-stranded

<400> SEQUENCE: 22
aatctagaga cattgtagcc attggggact tc 32

<210> SEQ ID NO 23
<211> LENGTH: 26
<212> TYPE: DNA
<213> ORGANISM: Artificial Sequence
<220> FEATURE:

<223> OTHER INFORMATION: single-stranded

<400> SEQUENCE: 23
tacattgtag ccatcgggga cttctc 26

<210> SEQ ID NO 24
<211> LENGTH: 24
<212> TYPE: DNA
<213> ORGANISM: Artificial Sequence
<220> FEATURE:
<223> OTHER INFORMATION: single-stranded

<400> SEQUENCE: 24
acctctgtgc agagaaccga tcac 24

<210> SEQ ID NO 25
<211> LENGTH: 23
<212> TYPE: DNA
<213> ORGANISM: Artificial Sequence
<220> FEATURE:
<223> OTHER INFORMATION: single-stranded

<400> SEQUENCE: 25
ccagtcctct ctgcagagaa gcg 23

<210> SEQ ID NO 26
<211> LENGTH: 22
<212> TYPE: DNA
<213> ORGANISM: Artificial Sequence
<220> FEATURE:
<223> OTHER INFORMATION: single-stranded

<400> SEQUENCE: 26
tcaggcctga ctgcaaagaa cc 22

<210> SEQ ID NO 27
<211> LENGTH: 22
<212> TYPE: DNA
<213> ORGANISM: Artificial Sequence
<220> FEATURE:
<223> OTHER INFORMATION: single-stranded

<400> SEQUENCE: 27
ctctgcagag aaccgaccac tg 22

<210> SEQ ID NO 28
<211> LENGTH: 29
<212> TYPE: DNA
<213> ORGANISM: Artificial Sequence
<220> FEATURE:
<223> OTHER INFORMATION: single-stranded

<400> SEQUENCE: 28
acctctctgt ggagaattga tcactgagc 29

<210> SEQ ID NO 29
<211> LENGTH: 22
<212> TYPE: DNA
<213> ORGANISM: Artificial Sequence
<220> FEATURE:
<223> OTHER INFORMATION: single-stranded

<400> SEQUENCE: 29
cctcaggcct ctctgcagag aa 22

<210> SEQ ID NO 30
<211> LENGTH: 25
<212> TYPE: DNA
<213> ORGANISM: Artificial Sequence
<220> FEATURE:
<223> OTHER INFORMATION: single-stranded

<400> SEQUENCE: 30
tttctgcaaa gaagcgatca ctggg 25

<210> SEQ ID NO 31
<211> LENGTH: 23
<212> TYPE: DNA
<213> ORGANISM: Artificial Sequence
<220> FEATURE:
<223> OTHER INFORMATION: single-stranded

<400> SEQUENCE: 31
agatccctta ggcctctctg cag 23

<210> SEQ ID NO 32
<211> LENGTH: 33
<212> TYPE: DNA
<213> ORGANISM: Artificial Sequence
<220> FEATURE:
<223> OTHER INFORMATION: single-stranded

<400> SEQUENCE: 32
cttgagcttg tttccagaga cattgtaccc ttc 33

<210> SEQ ID NO 33
<211> LENGTH: 31
<212> TYPE: DNA
<213> ORGANISM: Artificial Sequence
<220> FEATURE:
<223> OTHER INFORMATION: single-stranded

<400> SEQUENCE: 33
ctcaagcttg tttcaagaaa cacagtaccc c 31

<210> SEQ ID NO 34
<211> LENGTH: 30
<212> TYPE: DNA
<213> ORGANISM: Artificial Sequence
<220> FEATURE:
<223> OTHER INFORMATION: single-stranded

<400> SEQUENCE: 34
gtttagttca gagtgcaagt cagggaactg 30

<210> SEQ ID NO 35
<211> LENGTH: 32
<212> TYPE: DNA
<213> ORGANISM: Artificial Sequence
<220> FEATURE:
<223> OTHER INFORMATION: single-stranded

<400> SEQUENCE: 35
ctgtagccat ctgagacttc tcctttgtta gt 32

<210> SEQ ID NO 36
<211> LENGTH: 27
<212> TYPE: DNA
<213> ORGANISM: Artificial Sequence
<220> FEATURE:
<223> OTHER INFORMATION: single-stranded

<400> SEQUENCE: 36
tagccatcgg ggacttctcc tttatct 27

<210> SEQ ID NO 37
<211> LENGTH: 35
<212> TYPE: DNA
<213> ORGANISM: Artificial Sequence
<220> FEATURE:
<223> OTHER INFORMATION: single-stranded

<400> SEQUENCE: 37
ctatagccat ctgagacttc tcctttgtca gtatc 35

<210> SEQ ID NO 38
<211> LENGTH: 29
<212> TYPE: DNA
<213> ORGANISM: Artificial Sequence
<220> FEATURE:
<223> OTHER INFORMATION: single-stranded

<400> SEQUENCE: 38
gagcctctct gcagaaaatc gatccttag 29

<210> SEQ ID NO 39
<211> LENGTH: 27
<212> TYPE: DNA
<213> ORGANISM: Artificial Sequence
<220> FEATURE:
<223> OTHER INFORMATION: single-stranded

<400> SEQUENCE: 39
acatcaggca tctgtgctga gaatcaa 27

<210> SEQ ID NO 40
<211> LENGTH: 24
<212> TYPE: DNA
<213> ORGANISM: Artificial Sequence
<220> FEATURE:
<223> OTHER INFORMATION: single-stranded

<400> SEQUENCE: 40
ccatcaggcc tctcagctga gaat 24

<210> SEQ ID NO 41
<211> LENGTH: 30
<212> TYPE: DNA
<213> ORGANISM: Artificial Sequence
<220> FEATURE:
<223> OTHER INFORMATION: single-stranded

<400> SEQUENCE: 41
gcattaggca tcttagctga gaatcgatcc 30

<210> SEQ ID NO 42
<211> LENGTH: 28
<212> TYPE: DNA
<213> ORGANISM: Artificial Sequence
<220> FEATURE:
<223> OTHER INFORMATION: single-stranded

<400> SEQUENCE: 42
taaagttgca tcaggcatct ctgctgag 28

<210> SEQ ID NO 43
<211> LENGTH: 29

<212> TYPE: DNA
<213> ORGANISM: Artificial Sequence
<220> FEATURE:
<223> OTHER INFORMATION: single-stranded

<400> SEQUENCE: 43
actgaactgt tgagctgaga atcgatcag 29

<210> SEQ ID NO 44
<211> LENGTH: 26
<212> TYPE: DNA
<213> ORGANISM: Artificial Sequence
<220> FEATURE:
<223> OTHER INFORMATION: single-stranded

<400> SEQUENCE: 44
atacgtccct ccagtccttt cagcta 26

<210> SEQ ID NO 45
<211> LENGTH: 24
<212> TYPE: DNA
<213> ORGANISM: Artificial Sequence
<220> FEATURE:
<223> OTHER INFORMATION: single-stranded

<400> SEQUENCE: 45
agaaagaagt gttcggcctc ctgg 24

<210> SEQ ID NO 46
<211> LENGTH: 25
<212> TYPE: DNA
<213> ORGANISM: Artificial Sequence
<220> FEATURE:
<223> OTHER INFORMATION: single-stranded

<400> SEQUENCE: 46
agggtgaatt tgggaggcac ttagc 25

<210> SEQ ID NO 47
<211> LENGTH: 26
<212> TYPE: DNA
<213> ORGANISM: Artificial Sequence
<220> FEATURE:
<223> OTHER INFORMATION: single-stranded

<400> SEQUENCE: 47
acgttccgtt aggtctttca gctgtg 26

<210> SEQ ID NO 48
<211> LENGTH: 24
<212> TYPE: DNA
<213> ORGANISM: Artificial Sequence
<220> FEATURE:
<223> OTHER INFORMATION: single-stranded

<400> SEQUENCE: 48
ggccctcttt gggaaattca gcag 24

<210> SEQ ID NO 49
<211> LENGTH: 20
<212> TYPE: DNA
<213> ORGANISM: Artificial Sequence
<220> FEATURE:
<223> OTHER INFORMATION: single-stranded

<400> SEQUENCE: 49
cccgagagac gctgtaccct 20

<210> SEQ ID NO 50
<211> LENGTH: 23
<212> TYPE: DNA
<213> ORGANISM: Artificial Sequence
<220> FEATURE:
<223> OTHER INFORMATION: single-stranded

<400> SEQUENCE: 50
tgtcagagtg gacaaggtca ggc 23

<210> SEQ ID NO 51
<211> LENGTH: 27
<212> TYPE: DNA
<213> ORGANISM: Artificial Sequence
<220> FEATURE:
<223> OTHER INFORMATION: single-stranded

<400> SEQUENCE: 51
tggagcattg ggctaaaaat cgctcat 27

<210> SEQ ID NO 52
<211> LENGTH: 24
<212> TYPE: DNA
<213> ORGANISM: Artificial Sequence
<220> FEATURE:
<223> OTHER INFORMATION: single-stranded

<400> SEQUENCE: 52
ctcttggcag acacgtagcc ttca 24

<210> SEQ ID NO 53
<211> LENGTH: 24
<212> TYPE: DNA
<213> ORGANISM: Artificial Sequence
<220> FEATURE:
<223> OTHER INFORMATION: single-stranded

<400> SEQUENCE: 53
gcgttcttgg ggcattgaga tgag 24

<210> SEQ ID NO 54
<211> LENGTH: 31
<212> TYPE: DNA
<213> ORGANISM: Artificial Sequence
<220> FEATURE:
<223> OTHER INFORMATION: single-stranded

<400> SEQUENCE: 54
tgtcgagaga cactgtatcc atcagagatc t 31

<210> SEQ ID NO 55
<211> LENGTH: 34
<212> TYPE: DNA
<213> ORGANISM: Artificial Sequence
<220> FEATURE:
<223> OTHER INFORMATION: single-stranded

<400> SEQUENCE: 55
tattctggag actgttgact cagaggaaag atct 34

<210> SEQ ID NO 56
<211> LENGTH: 35
<212> TYPE: DNA
<213> ORGANISM: Artificial Sequence
<220> FEATURE:
<223> OTHER INFORMATION: single-stranded

<400> SEQUENCE: 56
catgataccc ctcagagata tctccttttt cagtg 35

<210> SEQ ID NO 57
<211> LENGTH: 31
<212> TYPE: DNA
<213> ORGANISM: Artificial Sequence
<220> FEATURE:
<223> OTHER INFORMATION: single-stranded

<400> SEQUENCE: 57
cttttcgaga gactttgtac ccttcaggaa c 31

<210> SEQ ID NO 58
<211> LENGTH: 27
<212> TYPE: DNA
<213> ORGANISM: Artificial Sequence
<220> FEATURE:
<223> OTHER INFORMATION: single-stranded

<400> SEQUENCE: 58
tctctctaga gacactgtac ccctcag 27

<210> SEQ ID NO 59
<211> LENGTH: 25
<212> TYPE: DNA
<213> ORGANISM: Artificial Sequence
<220> FEATURE:
<223> OTHER INFORMATION: single-stranded

<400> SEQUENCE: 59
ttgagaatgt taggtttggg cggct 25

<210> SEQ ID NO 60
<211> LENGTH: 18
<212> TYPE: DNA
<213> ORGANISM: Artificial Sequence
<220> FEATURE:
<223> OTHER INFORMATION: single-stranded

<400> SEQUENCE: 60
tgaactgccg gtcctggg 18

<210> SEQ ID NO 61
<211> LENGTH: 40
<212> TYPE: DNA
<213> ORGANISM: Artificial Sequence
<220> FEATURE:
<223> OTHER INFORMATION: single-stranded

<400> SEQUENCE: 61
tgccaggaaa tattttcaat agggatatgt ctctaatcaa 40

<210> SEQ ID NO 62
<211> LENGTH: 31
<212> TYPE: DNA
<213> ORGANISM: Artificial Sequence
<220> FEATURE:
<223> OTHER INFORMATION: single-stranded

<400> SEQUENCE: 62
gttagaatga ctatgctgac tcagggcatc t 31

<210> SEQ ID NO 63
<211> LENGTH: 22
<212> TYPE: DNA
<213> ORGANISM: Artificial Sequence
<220> FEATURE:
<223> OTHER INFORMATION: single-stranded

<400> SEQUENCE: 63
ccttcataga ccaatttaga ag 22

<210> SEQ ID NO 64
<211> LENGTH: 29
<212> TYPE: DNA
<213> ORGANISM: Artificial Sequence
<220> FEATURE:
<223> OTHER INFORMATION: single-stranded

<400> SEQUENCE: 64
gtcttaccta caactgtgag tctggtgcc 29

<210> SEQ ID NO 65
<211> LENGTH: 28
<212> TYPE: DNA
<213> ORGANISM: Artificial Sequence
<220> FEATURE:
<223> OTHER INFORMATION: single-stranded

<400> SEQUENCE: 65
ccttacctac aacggttaac ctggtccc 28

<210> SEQ ID NO 66
<211> LENGTH: 31
<212> TYPE: DNA
<213> ORGANISM: Artificial Sequence
<220> FEATURE:
<223> OTHER INFORMATION: single-stranded

<400> SEQUENCE: 66
cttactcacc tacaacagtg agccaacttc c 31

<210> SEQ ID NO 67
<211> LENGTH: 26
<212> TYPE: DNA
<213> ORGANISM: Artificial Sequence
<220> FEATURE:
<223> OTHER INFORMATION: single-stranded

<400> SEQUENCE: 67
atacccaaga cagagagctg ggttcc 26

<210> SEQ ID NO 68
<211> LENGTH: 29
<212> TYPE: DNA
<213> ORGANISM: Artificial Sequence
<220> FEATURE:
<223> OTHER INFORMATION: single-stranded

<400> SEQUENCE: 68
aacttaccta ggatggagag tcgagtccc 29

<210> SEQ ID NO 69
<211> LENGTH: 22
<212> TYPE: DNA
<213> ORGANISM: Artificial Sequence
<220> FEATURE:
<223> OTHER INFORMATION: single-stranded

<400> SEQUENCE: 69
ctgtcacagt gagcctggtc cc 22

<210> SEQ ID NO 70
<211> LENGTH: 18
<212> TYPE: DNA
<213> ORGANISM: Artificial Sequence
<220> FEATURE:
<223> OTHER INFORMATION: single-stranded

<400> SEQUENCE: 70
cacggtgagc cgtgtccc 18

<210> SEQ ID NO 71
<211> LENGTH: 22
<212> TYPE: DNA
<213> ORGANISM: Artificial Sequence
<220> FEATURE:
<223> OTHER INFORMATION: single-stranded

<400> SEQUENCE: 71
ccagtacggt cagcctagag cc 22

<210> SEQ ID NO 72
<211> LENGTH: 18
<212> TYPE: DNA
<213> ORGANISM: Artificial Sequence
<220> FEATURE:
<223> OTHER INFORMATION: single-stranded

<400> SEQUENCE: 72
cactgtcagc cgggtgcc 18

<210> SEQ ID NO 73
<211> LENGTH: 18
<212> TYPE: DNA
<213> ORGANISM: Artificial Sequence
<220> FEATURE:
<223> OTHER INFORMATION: single-stranded

<400> SEQUENCE: 73
cactgagagc cgggtccc 18

<210> SEQ ID NO 74
<211> LENGTH: 17
<212> TYPE: DNA
<213> ORGANISM: Artificial Sequence
<220> FEATURE:
<223> OTHER INFORMATION: single-stranded

<400> SEQUENCE: 74
accaggagcc gcgtgcc 17

<210> SEQ ID NO 75
<211> LENGTH: 18
<212> TYPE: DNA
<213> ORGANISM: Artificial Sequence
<220> FEATURE:
<223> OTHER INFORMATION: single-stranded

<400> SEQUENCE: 75
cacggtcagc ctgctgcc 18

<210> SEQ ID NO 76

```
<211> LENGTH: 18
<212> TYPE: DNA
<213> ORGANISM: Artificial Sequence
<220> FEATURE:
<223> OTHER INFORMATION: single-stranded

<400> SEQUENCE: 76

gaccgtgagc ctggtgcc                                                18
```